(12) United States Patent
Vargas et al.

(10) Patent No.: US 9,808,597 B2
(45) Date of Patent: Nov. 7, 2017

(54) SHAPE-TRANSFERRING CANNULA SYSTEM AND METHOD OF USE

(75) Inventors: Jaime S. Vargas, Redwood City, CA (US); Scott Berggren, Oakland, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1087 days.

(21) Appl. No.: 13/087,156

(22) Filed: Apr. 14, 2011

(65) Prior Publication Data

US 2011/0282149 A1 Nov. 17, 2011

Related U.S. Application Data

(63) Continuation of application No. 11/479,704, filed on Jun. 30, 2006, now Pat. No. 7,947,000, which is a continuation-in-part of application No. 10/661,159, filed on Sep. 12, 2003, now Pat. No. 8,298,161.

(60) Provisional application No. 60/409,927, filed on Sep. 12, 2002.

(51) Int. Cl.
*A61M 25/00* (2006.01)
*A61M 25/01* (2006.01)

(52) U.S. Cl.
CPC .... *A61M 25/0021* (2013.01); *A61M 25/0105* (2013.01); *A61M 25/0136* (2013.01); *A61M 25/0138* (2013.01); *A61M 25/0147* (2013.01); *A61M 25/0155* (2013.01); *A61M 25/0158* (2013.01); *A61M 2025/0058* (2013.01); *Y10T 29/49826* (2015.01)

(58) Field of Classification Search
CPC .......... A61M 25/0021; A61M 25/0105; A61M 25/0136; A61M 25/0138

USPC .................. 600/587, 104, 114, 141; 604/514
See application file for complete search history.

(56) References Cited

U.S. PATENT DOCUMENTS

| 616,672 | A | | 12/1898 | Kelling |
|---|---|---|---|---|
| 2,421,279 | A | | 5/1947 | Marty |
| 2,510,198 | A | | 6/1950 | Tesmer |
| 3,096,962 | A | | 7/1963 | Meijs |
| 3,642,277 | A | * | 2/1972 | Gersten .......................... 482/37 |
| 4,048,749 | A | * | 9/1977 | Zitting et al. ................. 446/363 |
| 4,161,998 | A | * | 7/1979 | Trimble ...................... 182/190 |
| 4,294,233 | A | | 10/1981 | Takahashi |
| 4,601,283 | A | | 7/1986 | Chikama |
| 4,753,223 | A | | 6/1988 | Bremer |
| 4,815,450 | A | | 3/1989 | Patel |
| 4,890,602 | A | | 1/1990 | Hake |
| 4,909,787 | A | | 3/1990 | Danforth |
| 5,174,276 | A | | 12/1992 | Crockard |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Sean Dougherty
(74) *Attorney, Agent, or Firm* — Jones Robb, PLLC

(57) ABSTRACT

The present invention is directed to a novel shape-transferring cannula system, which provides access to tortuous and unsupported paths. The shape-transferring cannula system and method enables exploration of hollow body structures, and creates a custom-contoured access port for insertion and removal of, for example, diagnostic, surgical, or interventional instruments to and from a site within the body to which the physician does not have line-of-sight access.

34 Claims, 29 Drawing Sheets

(56) References Cited

U.S. PATENT DOCUMENTS

| | | | |
|---|---|---|---|
| 5,251,611 A | 10/1993 | Zehel et al. | |
| 5,337,733 A | 8/1994 | Bauerfeind et al. | |
| 5,372,587 A | 12/1994 | Hammerslag et al. | |
| 5,482,029 A | 1/1996 | Sekiguchi et al. | |
| 5,681,260 A | 10/1997 | Ueda et al. | |
| 5,759,151 A | 6/1998 | Sturges | |
| 5,766,163 A | 6/1998 | Mueller et al. | |
| 5,779,624 A | 7/1998 | Chang | |
| 5,820,163 A | 10/1998 | Thacker et al. | |
| 5,855,565 A | 1/1999 | Bar-Cohen et al. | |
| 5,911,714 A | 6/1999 | Wenstrom, Jr. | |
| 5,916,146 A | 6/1999 | Allotta et al. | |
| 5,916,147 A | 6/1999 | Boury | |
| 5,921,915 A | 7/1999 | Aznoian et al. | |
| 5,944,690 A | 8/1999 | Falwell et al. | |
| 5,951,600 A * | 9/1999 | Lemelson | A61K 9/0009 623/2.11 |
| 5,976,074 A | 11/1999 | Moriyama | |
| 5,976,146 A | 11/1999 | Ogawa et al. | |
| 6,007,519 A | 12/1999 | Rosselli | |
| 6,071,234 A | 6/2000 | Takada | |
| 6,090,121 A | 7/2000 | Weber et al. | |
| 6,146,355 A | 11/2000 | Biggs | |
| 6,206,872 B1 | 3/2001 | Lafond et al. | |
| 6,327,492 B1 * | 12/2001 | Lemelson | A61B 17/320758 600/434 |
| 6,344,038 B1 | 2/2002 | Weber | |
| 6,468,203 B2 | 10/2002 | Belson | |
| 6,514,237 B1 | 2/2003 | Maseda | |
| 6,581,889 B2 | 6/2003 | Carpenter et al. | |
| 6,666,847 B2 | 12/2003 | Secrest et al. | |
| 6,679,836 B2 | 1/2004 | Couvillon et al. | |
| 6,684,552 B1 * | 2/2004 | Anders, III | 43/3 |
| 6,773,327 B1 * | 8/2004 | Felice et al. | 446/330 |
| 6,969,395 B2 | 11/2005 | Eskuri | |
| 6,974,411 B2 | 12/2005 | Belson | |
| 7,063,671 B2 | 6/2006 | Couvillon, Jr. | |
| 7,947,000 B2 | 5/2011 | Vargas et al. | |
| 8,298,161 B2 | 10/2012 | Vargas | |
| 8,771,224 B2 | 7/2014 | Vargas | |
| 8,894,564 B2 | 11/2014 | Vargas | |
| 9,402,626 B2 * | 8/2016 | Ortiz | A61B 17/068 |
| 2003/0069474 A1 | 4/2003 | Couvillon et al. | |
| 2003/0229332 A1 | 12/2003 | Intoccia | |
| 2003/0233025 A1 | 12/2003 | Saadat et al. | |
| 2003/0233026 A1 | 12/2003 | Saadat et al. | |
| 2003/0233027 A1 | 12/2003 | Ewers et al. | |
| 2003/0233057 A1 | 12/2003 | Saadat et al. | |
| 2003/0233058 A1 | 12/2003 | Ewers et al. | |
| 2003/0233066 A1 | 12/2003 | Ewers et al. | |
| 2004/0002665 A1 * | 1/2004 | Parihar | A43B 3/0005 600/587 |
| 2009/0065067 A1 * | 3/2009 | Bushman et al. | 137/217 |
| 2013/0090598 A1 | 4/2013 | Vargas | |
| 2014/0228642 A1 | 8/2014 | Vargas | |
| 2014/0288568 A1 | 9/2014 | Vargas | |
| 2014/0296779 A1 | 10/2014 | Vargas | |

* cited by examiner

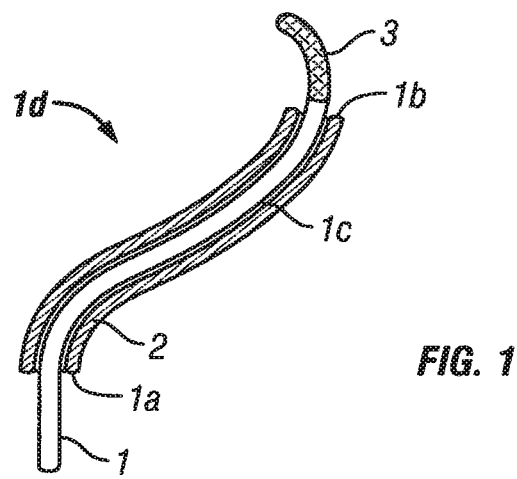
FIG. 1
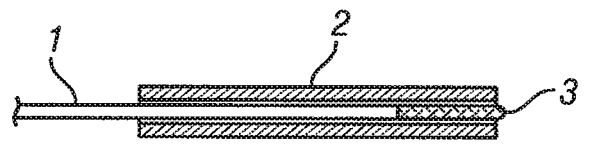
FIG. 2A
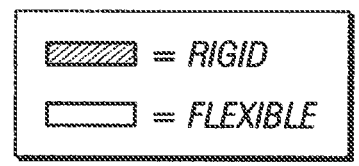
= RIGID
= FLEXIBLE
FIG. 2B
FIG. 2C
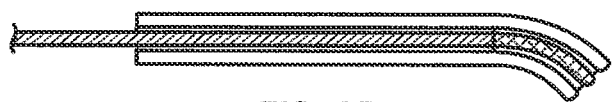
FIG. 2D

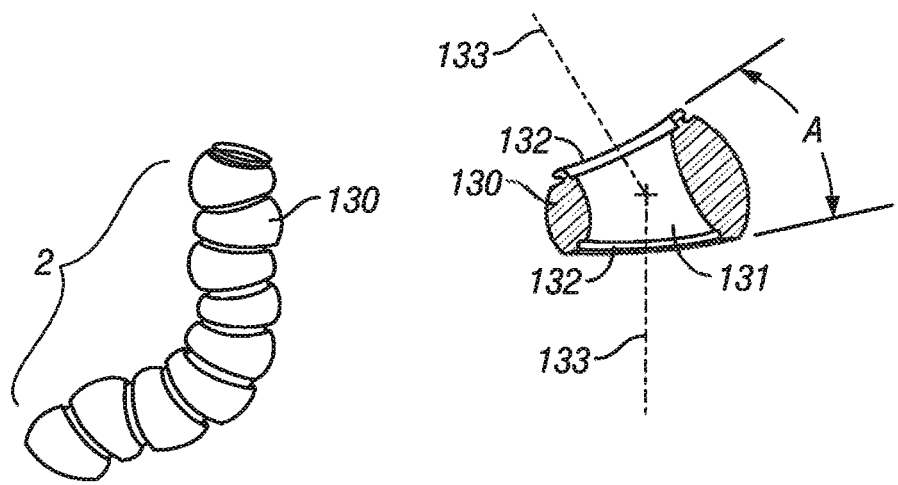
FIG. 13A
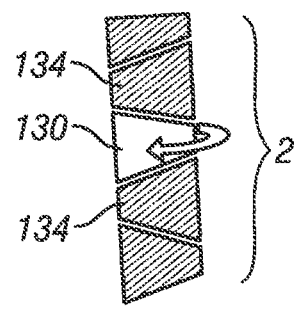     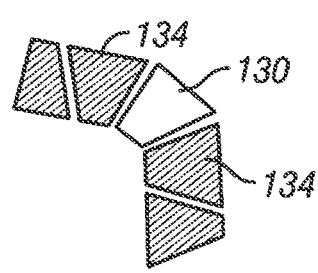
FIG. 13B          FIG. 13C

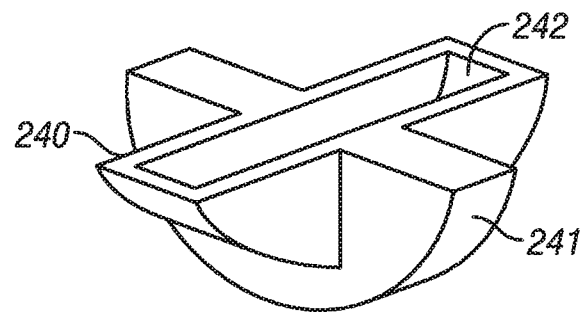
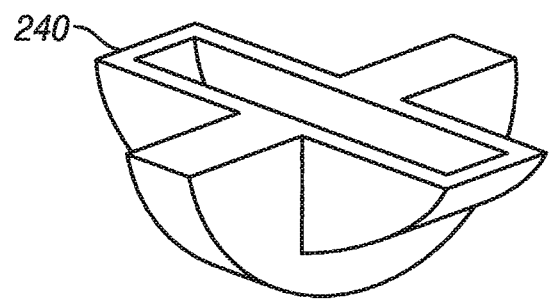
FIG. 21
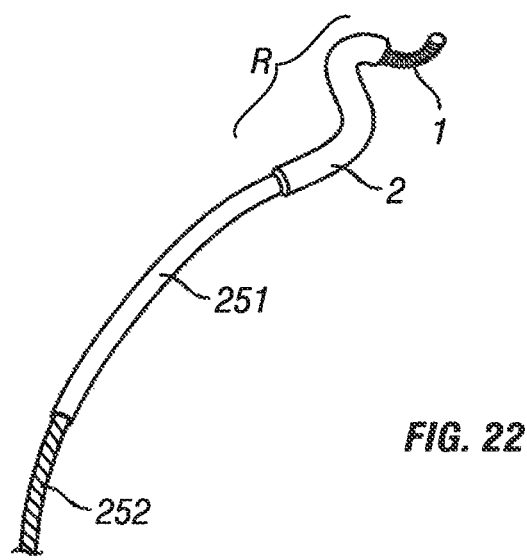
FIG. 22

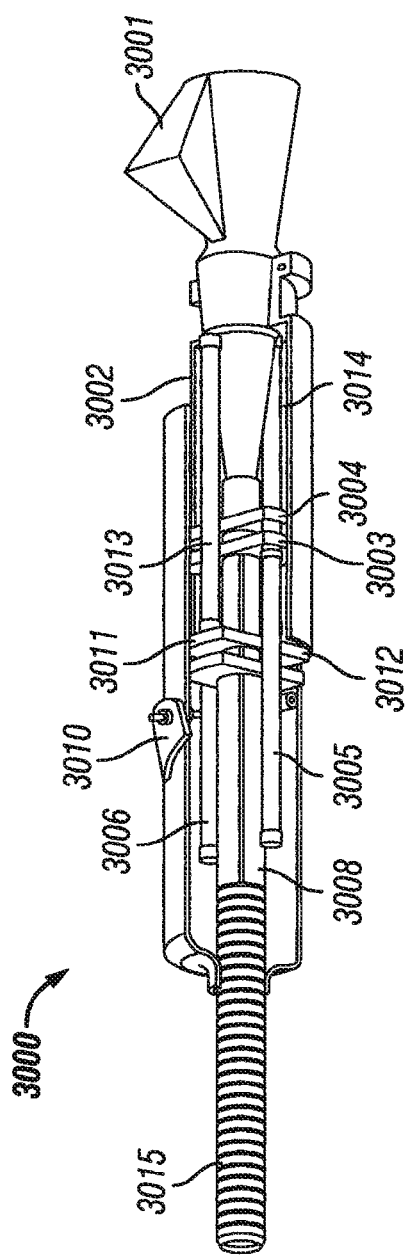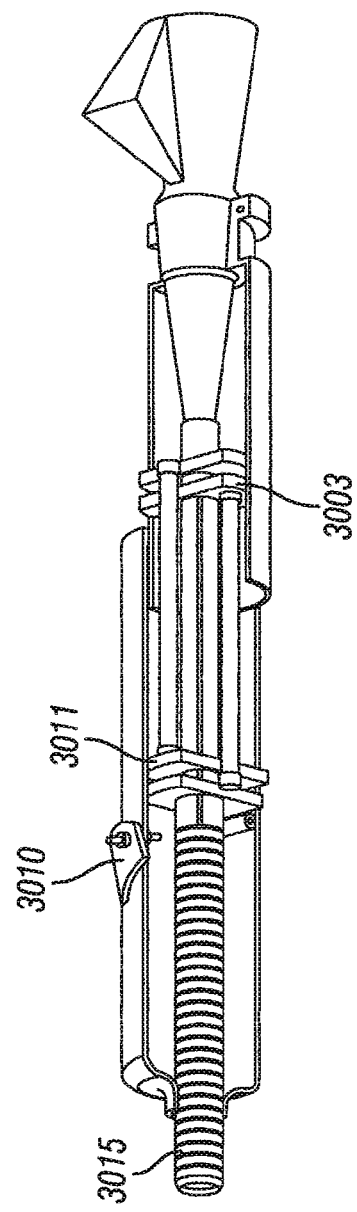
FIG. 30A
FIG. 30B

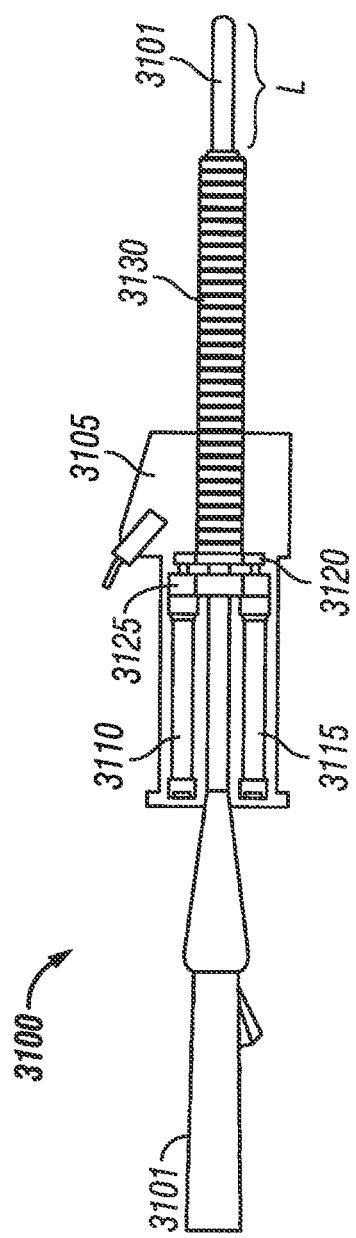
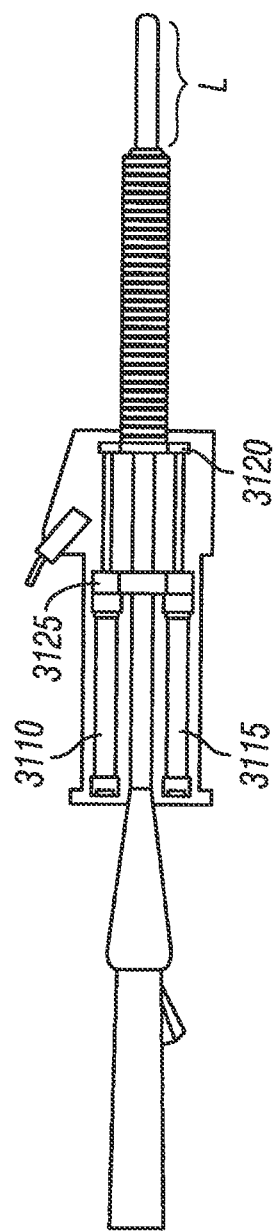
FIG. 31A
FIG. 31B

3200

AXIALLY SLIDE AN ENDOSCOPE WITH RESPECT TO A CANNULA SYSTEM HAVING A REFERENCE FRAME HANDLE AND A RIGIDIZABLE LINKAGE TO EXPOSE A SPECIFIC LENGTH OF A TIP OF THE ENDOSCOPE AND ESTABLISH A RELATIVE POSITION BETWEEN THE ENDOSCOPE AND THE REFERENCE FRAME HANDLE — 3205

ACTIVATE ACTUATORS COUPLED TO THE REFERENCE FRAME HANDLE TO RIGIDIZE THE RIGIDIZABLE LINKAGE WHILE MAINTAINING THE EXPOSED TIP LENGTH AND THE RELATIVE POSITION BETWEEN THE ENDOSCOPE AND THE REFERENCE FRAME HANDLE — 3210

FIG. 32

SHAPE-TRANSFERRING CANNULA SYSTEM AND METHOD OF USE

RELATED U.S. PATENT APPLICATION

This application is a continuation of U.S. patent application Ser. No. 11/479,704 (filed Jun. 30, 2006; now U.S. Pat. No. 7,947,000 B2), which is a continuation-in-part of U.S. patent application Ser. No. 10/661,159 (filed Sep. 12, 2003; currently pending), which claims the benefit of priority of U.S. Provisional Application No. 60/409,927 (filed Sep. 12, 2002). This application is also related to U.S. patent application Ser. No. 10/899,561 (for "Cannula System and Method of Use" (filed Jul. 27, 2004), the entirely of which is incorporated herein by reference.

FIELD OF THE INVENTION

The present invention relates to devices, systems, and processes useful for exploration of hollow body structures, particularly those areas accessed through a tortuous, unsupported path. More particularly, the present invention relates to a shape-transferring cannula device that creates a custom-contoured access port for insertion and removal of diagnostic, surgical, or interventional instruments to and from a site within the body to which the physician does not have line-of-sight access.

BACKGROUND OF THE INVENTION

Surgical cannulas are well known in the art. Such devices generally include tube-like members that are inserted into openings made in the body so as to line the openings and maintain them against closure. Surgical cannulae can be used for a wide variety of purposes, and their particular construction tends to vary accordingly (see, e.g., U.S. Pat. No. 5,911,714). Flexible endoscopes, endovascular catheters and guidewires, and trocar cannulae such as those used in laparascopic surgery, are examples of such devices. Several U.S. patents recite such devices. See, for example, U.S. Pat. Nos. 5,482,029; 5,681,260; 5,766,163; 5,820,623; 5,921, 915; 5,976,074; 5,976,146; 6,007,519; 6,071,234; and 6,206,872.

All of these devices are in use in one form or another and they are helpful to some extent, but they also pose several problems. Flexible endoscopes and endovascular catheters rely on reaction forces generated by pushing against the tissue of the body cavity being explored to navigate around corners or bends in the anatomy. This approach works reasonably well for small-diameter endovascular catheters that are typically run through arteries well supported by surrounding tissue. In this case the tissue is effectively stiffer than the catheter or guidewire and is able to deflect the catheter's path upon advancement into the vessel. The approach is much less successful in the case of flexible endoscopes being guided through a patient's colon or stomach. In these cases the endoscope is either significantly stiffer than the body cavity tissue it is being guided through or, as is the case for the stomach or an insufflated abdomen, the body cavity is sufficiently spacious that the endoscope has no walls at all to guide it. In the case of colonoscopy, the endoscope forces the anatomy to take painful, unnatural shapes. Often, the endoscope buckles and forms "loops" when the colonoscopist attempts to traverse tight corners. Pushing on the end of the flexible endoscope tends to grow the loop rather than advance the endoscope. "Pushing through the loop" relies on the colon to absorb potentially damaging shapes of force to advance the endoscope. In cases of unusually tortuous anatomy, the endoscope may not reach its intended target at all, leaving the patient at risk of undiagnosed and potentially cancerous polyps.

Endovascular catheters have drawbacks as well. While generally flexible enough to avoid seriously damaging the vessel's endothelial surface, guidewires are difficult to guide into small side branches of large vessels such as the coronary ostia or into relatively small vessels connecting to relatively large chambers such as the pulmonary veins. Catheters are even more limited in their ability to deal with greatly tortuous vessel anatomy such as the vessels radiating from the brain's so-called Circle of Willis.

U.S. Pat. No. 5,251,611 (Zehel) discloses the use of one or more rigidizable conduits for conducting exploratory procedures. A particular rigidizable conduit disclosed by Zehel includes a series of nested segments that are traversed by a plurality of cables or wires. Tension is applied to the wires to press the segments together, thereby producing a stiffened conduit. A side effect of the compression reaction to the applied tension is a shortening of the conduit as the segments are pressed together. For procedures involving an instrument that is inserted in the conduit, the shortening of the conduit will result in a change in the relative position of the instrument and the conduit. This change in relative position may have an adverse effect on the placement or use of the instrument.

Ablation and EKG mapping catheters used in cardiological electrophysiology find their intended targets chiefly by trial and error insertion and twisting of a guidewire/catheter accompanied by gross motions of the entire catheter. A need, therefore exists for a cannula system that provides access port for insertion and removal of diagnostic, surgical, or interventional instruments to and from a site within the body to which the physician does not have line-of-sight access. Furthermore, there is a need for cannula systems that can follow a tortuous path through hollow soft-tissue structures without relying on the surrounding tissue to mechanically support and guide its insertion and may be steered and advanced directly to an anatomical point of interest. There is also a need for a cannula system that can accommodate shortening in the cannula and maintain a relative position between the cannula and an instrument inserted therein as well as between the cannula and a target site within the body.

BRIEF DESCRIPTION OF THE DRAWINGS

FIG. 1 is a diagrammatic sectional view of the shape transferring cannula system illustrating the major components.

FIGS. 2A-2C illustrate diagrammatic sectional representations of a sequence of rigidizing structure stiffening, relaxing, and advancement that enables guiding of the shape transferring cannula.

FIGS. 13A-13C is a perspective view of a rotating link cannula structure

FIG. 21 is a perspective view of two-axis pivoting links.

FIG. 22 depicts a catheter with a shape-transferring section.

FIG. 30A depicts an endoscope with handle and actuators for dual cannula system in an extended configuration.

FIG. 30B depicts an endoscope with handle and actuators for dual cannula system in a retracted configuration.

FIG. 31A depicts a cannula system with an endoscope and reference frame handle in a relaxed configuration.

FIG. 31B depicts a cannula system with an endoscope and reference frame handle in a rigidized configuration.

FIG. 32 depicts a flow diagram of a method embodiment in accordance with the present invention.

DETAILED DESCRIPTION OF THE INVENTION

Figure 3:
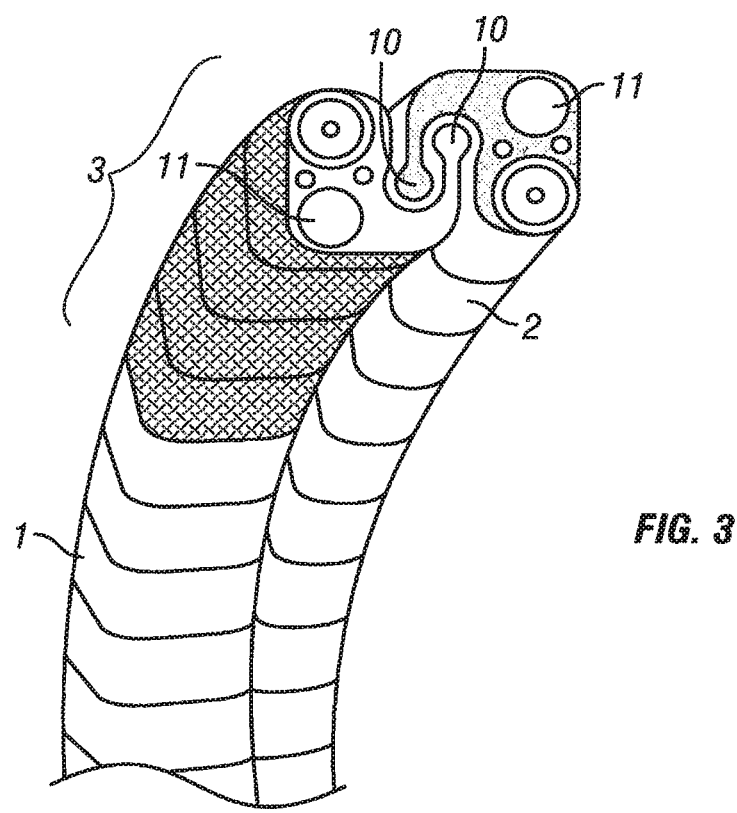
FIG. 3 is a perspective view of an embodiment of laterally parallel rigidizing core and sheath linkage structures.

The present invention is directed to a novel shape-transferring cannula system, which provides access to tortuous and unsupported paths. The shape-transferring cannula system and method enables exploration of hollow body structures, and creates a custom-contoured access port for insertion and removal of, for example, diagnostic, surgical, or interventional instruments to and from a site within the body to which the physician does not have line-of-sight access.

The shape-transferring cannula can follow a tortuous path through hollow soft-tissue structures without relying on the surrounding tissue to mechanically support and guide its insertion. The system includes two parallel rigidizing sections that alternatingly stiffen and relax with respect to one another and alternatingly transfer the path shape traced-out by the articulating tip to one another. A steerable articulated tip is attached to one of the rigidizing sections. The cannulas custom shape is formed by guiding the articulated tip along a desired path direction, stiffening the attached rigidizing section, and advancing the other rigidizing section along the stiffened section.

The end of the shape-transferring cannula may be steered and advanced directly to an anatomical point of interest. The user traces a path for the shape-transferring cannula with the steerable tip and in doing so defines the longitudinal shape assumed by the cannula, thus directing the working end of the cannula to a target site without substantially disturbing the length of cannula behind it. The ability to navigate predictably within heart chambers and swap out catheters from a relatively fixed position, for example, greatly improves electrophysiologists' ability to methodically locate and ablate the ectopic foci responsible for atrial fibrillation and other cardiac arrhythmias.

The ability to localize movements to the user-controlled tip of the cannula is especially valuable when working within particularly sensitive open structures such as the ventricles of the brain or loosely supported, tortuous structures such as the colon that provide very little mechanical support for intubation around corners.

The shape-transferring cannula system assumes the shape traced by the path of the articulating tip in an incremental fashion, with the core and sheath rigidizing structures transferring the traced path shape back and forth to each other. Having reached the target site, the external sheath can be made flexible and slid out over the rigidized central core. Unlike the lengthy re-intubation procedure for a conventional flexible endoscope, returning to the target site is simply a matter of sliding the sheath or surgical instruments over the core that now acts as a guidewire. Alternately, the sheath may be left rigid and in place once having reached the target site and the core may be made flexible and removed. This leaves the shaped sheath to act as a cannula through which surgical instruments such as snares, ultrasound probes, biopsy probes and other diagnostic devices, electrocautery tools, and the like may be transferred to and from the target site.

The individual elements of the invention have useful applications independent of the full system. For instance, the rigidizing sheath structure may be used on its own as a rigidizing cannula when introduced to a target site by a conventional guidewire, flexible endoscope, or similar introduction element. Unlike conventional rigid cannulae, the rigidizing cannula does not have a predetermined longitudinal shape. Yet, when stiffened, the rigidizing cannula may support reaction forces like a rigid cannula when tools are run down its length, thus protecting sensitive tissue structures.

The present invention will now be described in detail with reference to the following drawings. FIG. 1 depicts a preferred embodiment of a shape-transferring cannula system 1d having two parallel rigidizing core 1 and sheath 2 structures, a steerable articulated tip 3 attached to one of the rigidizing structures, a proximal end 1a, a distal end 1b and a lumen 1c through which surgical tools may be introduced or through which the target site may be irrigated or suctioned. The core 1 and sheath 2 are parallel structures that can be coaxial or side-by-side and that may be made rigid or flexible with respect to one another. The core and sheath structures may be unitary materials or continuous structures, or they can be formed of individual, flexibly connected rigid links. The core and sheath structure employs rigidizing cables which, when put into tension, pull the links together to increase friction between links and prevent relative motion between the links. The core's rigidizing structure is built-up of links such that a convex spherical surface on one link engages a concave surface on an adjacent link. The core's rigidizing cable runs through each core link's central orifice, connecting the entire core rigidizing structure. The core link's central orifice has a diameter D1 that is in the range from about 0.5 mm to about 30 mm. Those of skill in the art will readily appreciate that the particular application, e.g., device, to which the present invention is applied may require a particular diameter D1, and it is within the scope of the present invention to select an appropriate diameter D1 for the specific application. For example, a typical endoscope employing structures in accordance with the present invention may have an inner diameter from about ¼ inch to about ½ inch, although larger or smaller sizes may also be suitable.

The system employs a method of incremental advancement to deliver the distal end 1b of the cannula to a target site. The core 1 and sheath 2 rigidizing structures are alternatingly advanced, one structure past the other, the stationary structure being made rigid and acting as a guide for the advancing flexible structure. The steerable tip assembly 3 is located on the end of at least one of the two rigidizing structures such as the core 1 as depicted in FIG. 1. The steerable tip 3 may be actuated via cables or other tension members, magnetostrictive materials, bimetallic strips or other flexing elements, piezoelectric polymer films or ceramics, shape memory materials such as nickel-titanium shape memory alloys or shape memory polymers, electroactive artificial muscle polymers, or the like. The length of the steerable tip 3 and the length L, described elsewhere herein, are preferably mutually selected to be about the same length, so that the cannula can follow and track the steerable tip (see FIG. 12G).

The overall length of the cannula will vary according to the particular hollow body structure for which it is intended. For instance, used in a colonoscope application the shape-transfer cannula length might range from 100 cm to 180 cm. In a bronchoscope application the shape-transfer cannula length might range from about 30 cm to about 100 cm. In a catheter application, the rigidizing core 1 and sheath 2 components of a shape-transfer cannula might be limited to a relatively small section of the entire catheter length, as depicted in FIG. 22. For example, the core 1 and sheath 2 can be provided only at the distalmost end of the device or apparatus that is intended to be steered. In such a case the majority of the cannula's length include "passive" conventional extruded catheter material 251 and a non-rigidizing section of core 252. For example, in accessing particular areas within the heart's ventricles, the extra control provided by the shape-transferring core 1 and sheath 2 components might only be needed within the ventricles themselves so the length of the rigidizing section R, need only be sufficient to navigate within the ventricles themselves.

Another aspect of the present invention is that the distal, steerable portion of the apparatus has a shape-transforming length L and an outer diameter D, with the ratio UD being at least about 5 (L/D>5), so that there is enough longitudinal length of the shape-transforming portion of the device or apparatus to track the steerable tip 3.

FIG. 2 illustrates by way of example a sequence in which the core 1 and sheath 2 alternate sequentially between rigid and flexible such that the entire structure takes the shape traced by the steerable tip 3 as the shape-transferring cannula is inserted into a hollow body structure such as the colon, stomach, lung bronchi, uterus, abdominal cavity, brain ventricle, heart chamber, blood vessel, or the like. In FIG. 2a, the sheath 2 is rigid and the core 1 with steerable tip 3 is flexible. The steerable tip 3 initially lies within and is approximately flush with the distal end 1b of the sheath 2 such that both the sheath 2 and core 1 assume the same longitudinal shape whether curved or straight. To begin the sequence that advances and forms the longitudinal shape of the shaped cannula structure 1d, in FIG. 2b the core 1 is advanced distally through the rigidized sheath 2, exposing the length of the steerable tip 3. The user then directs the exposed steerable tip 3 in the desired direction of insertion and advances the structure with, for example, a squeeze advancement mechanism (which will be discussed later herein) or through a cam mechanism or through any other structure or mechanism that rigidizes and relaxes the core 1 and sheath 2 in proper sequence. Referring to FIG. 2c, to advance the entire shape-transferring cannula structure 1d, the core 1 is made rigid and then the sheath 2 is relaxed and, as shown in FIG. 2d, the sheath is advanced over the core 1 and steerable tip 3. Preferably, the longitudinal relative motion between the two rigidizing elements (i.e. core 1 and sheath 2) is limited to the length of the steerable tip 3, the user-controlled element that serves as the system's directional guide. The sheath 2 is then made rigid and the core 1 is relaxed and advanced to re-expose the steerable tip 3. Thus, in sequential fashion, the rigidizing structure portion of the shape-transferring cannula 1d takes the shape of the path traced by the steerable tip 3 as guided by the user.

Other sequences and combinations of stiffening, flexibility, and advancement to achieve the same result are possible within the scope of this invention. For instance, the sheath 2 and core 1 may be normally-stiff structures that momentarily become flexible at appropriate times in the shape-transferring cannula advancement sequence. In another example, the sheath 2 and core 1 may be normally-flexible structures that momentarily become rigid at appropriate times to complete the advancement sequence. In another example, the core 1 and sheath 2 may both include a steerable tip 3 providing each structure with both directional control and the momentary rigidity necessary for shape-transference FIG. 3 depicts an alternative embodiment of a shape-transferring cannula system in accordance with the present invention. In this embodiment, the shape-transferring core 1 and sheath 2 are not necessarily coaxial structures and may be laterally parallel structures that slidably engage each other longitudinally via engagement features 10. In general, engagement features in accordance with the present invention include structures that permit the core 1 and sheath 2 to slide or otherwise move longitudinally relative to each other. One aspect of engagement features in accordance with the present invention that one of the core 1 and sheath 2 provides a rail for advancement of the other of the core and sheath relative thereto.

At least one of the shape-transferring structures includes a steerable tip 3 with which to guide advancement of the system. Either or both of the shape-transferring structures can contain accessory lumens 11 through which surgical tools may be introduced or through which the target site may be irrigated or suctioned. The engagement feature 10 of either structure can be used as a guide for withdrawing samples or inserting tools that won't fit through the accessory lumen 11. Outsized tools may be provided with compatible engagement features such that they track along the guide formed by the rigidizing structure's engagement features.

In a preferred embodiment of the present invention, the user's selection of an advancement direction and his actuation of the system, whether manual or powered, causes the entire cycle of core rigidization, sheath relaxation, sheath advancement, sheath rigidization, and core relaxation to occur such that the structure is returned to its initial state with a new longitudinal shape.

The core and sheath structures may be unitary materials or continuous structures that can be transformed between relatively rigid and relatively flexible or they can be formed of individual, flexibly connected rigid links which become substantially locked together to rigidize the structure. In an embodiment comprised of links, the sheath and core linkage structures are rigidized by temporarily preventing, by any suitable mechanism, substantial relative motion between the links. For example, motion between links may be temporarily stopped or substantially reduced by tightening a tension cable to put the linkage into longitudinal compression, by electrostatic or magnetic forces, by hydraulic or pneumatic actuation, by changes in viscous coupling as with electrorheological or magnetorheological materials, or through any friction modulating means.

Figure 4A:
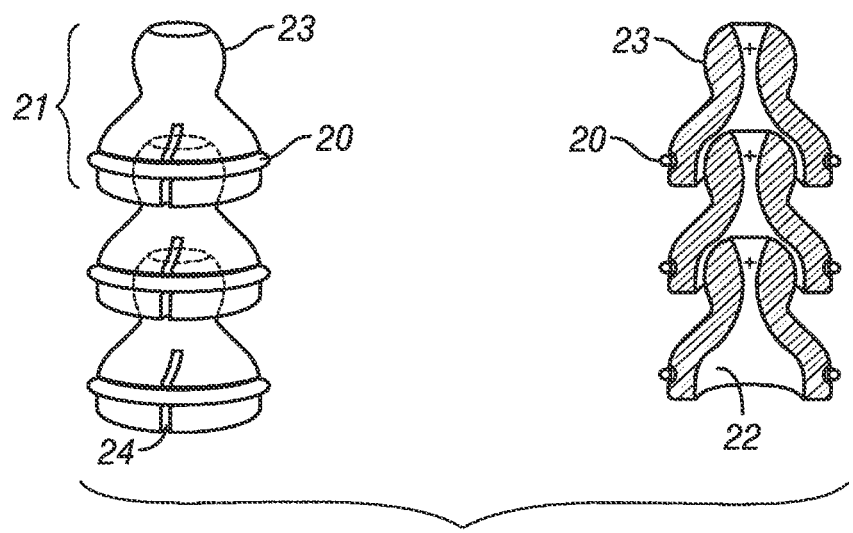
FIGS. 4A and 4B illustrate perspective views of captured-link rigidizing linkages.
Figure 4B:
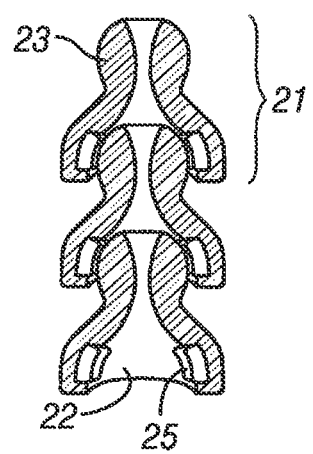

Linkages may be held together by a flexible internal cable or external covering, or by attaching the links to each other while leaving enough freedom of rotation to make the structure longitudinally flexible. More specifically as shown in FIGS. 4A and 4B, the links may be loosely captured by overlapping ball and cup features in adjacent links such that the cup features 22 overlap past the equators of the adjacent ball features 23. This arrangement allows two-axis pivoting between links while keeping the linkage intact. FIG. 4A illustrates a specific example of a rigidizing mechanism where sheath and core rigidizing linkage structures may include a compression element 20 in each link, such as a loop of nickel-titanium alloy wire or shape memory polymer whose shape-memory transition temperature is higher than normal body temperatures. A slot 24 in the cup 22 may facilitate compression of the cup against the ball 23 when the compression element 20 is actuated. The compression elements 20 in the links may be actuated through electrical or inductive heating or through any suitable means to activate the shape-memory effect such that the compression elements reduce their unstressed diameters, creating local compression between ball and cup, and thus increasing friction between links.

FIG. 4B illustrates another example of a rigidizing mechanism employing the same type of captured-link linkage configuration as the previous example. In this embodiment, either the ball 23 or the cup 22 can include active material components 25 made of materials such as electroactive polymer (EAP) that change shape when energized. The active material components may be oriented to expand radially when energized, causing interference between the ball and cup of adjacent links. Alternately, in a normally-rigid structure, the active material components 25 may be oriented to contract radially when energized, relieving interference between the ball and cup features of adjacent links.

By way of another example, linkages built of links made of dielectric materials may be rigidized electrostatically by building attractive or repulsive charges between links and increasing friction between links. By way of another example, inducing magnetic attraction or repulsion between links containing ferromagnetic materials can stiffen a rigidizing linkage by increasing friction between the links. By way of another example, linkages built with links made of conductive materials may be rigidized by inducing eddy currents that attract links to each other and increase friction between links.

Figure 5:
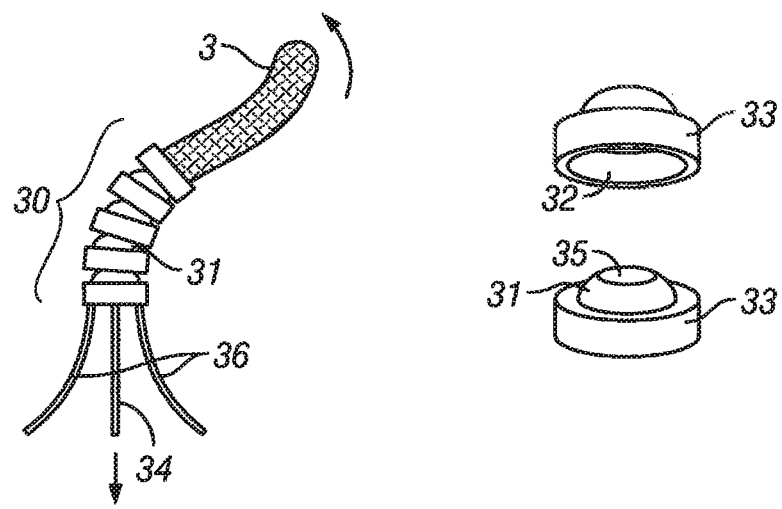
FIG. 5 is a perspective view of a cable-rigidized core linkage.
Figure 6:
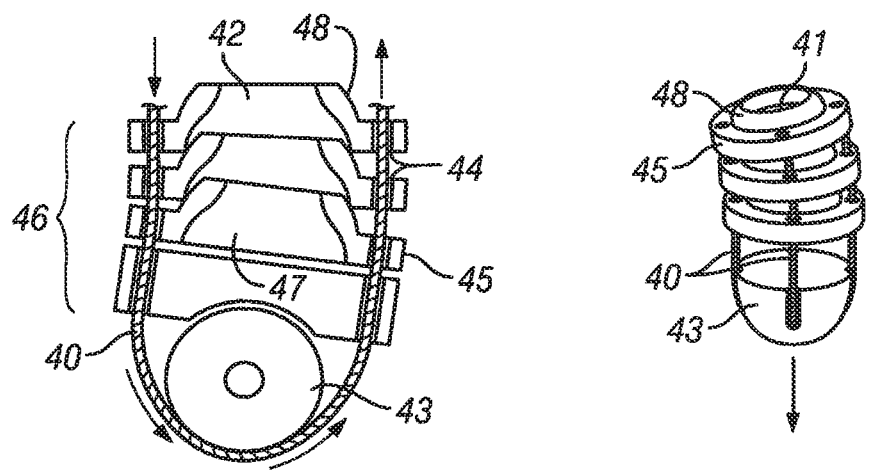
FIG. 6 shows perspective and sectional views of a cable-rigidized sheath linkage.

FIGS. 5 and 6 illustrate a linkage embodiment of parallel rigidizing sheath and core structure that employs rigidizing wires or cables 34 and 40, which go through the core 1 and sheath 2 respectively. These cables, when put into tension, pull the links together to increase friction between the links and thus prevent relative motion between the links. When not in tension, the rigidizing cables serve to hold the individual links in the rigidizing assembly together.

As illustrated in FIG. 5, the cores rigidizing structure 30 is built-up of links such that a convex spherical surface 31 on one link engages a concave surface 32 on the adjacent link. FIG. 5 shows cup-like nesting links 33 with a spherical ball-joint-like interface that allows two-axis pivoting between abutting links, thus making the linkage longitudinally flexible. The core's rigidizing cable 34 runs through each core link's central orifice 35, connecting the entire core rigidizing structure 30. The steerable tip 3 control cables 36 may also run through each link's central orifice 35. The control cables 36 may be mechanical cables transmitting tension or compression, or electrical connections transmitting power or signal to actuate or control the steerable tip 3. Alternatively, the rigidizing cable 34 and tip-steering cable 36 may be contained within individual lumens of a multi-lumen housing or within individual housings, keeping them separated and keeping the tip-steering cables 36 from binding when the rigidizing cable 34 is tensioned to stiffen the core structure. The housing material may be chosen for low friction cable movement. One lumen of the multilumen housing might also serve to guide the core 1 along a conventional guidewire for rapid insertion into guidewire accessible anatomy such as the atria and ventricles of the heart.

Other linkage geometries that allow two-axis pivoting are possible within the scope of this invention. For example as in FIG. 21, links 240 with male 241 and female 242 pivot features that each rotate on only one axis can be alternated and mounted within each other, within the rigidizing structure, with adjacent pivot features having axes perpendicular to one another. Thus, each pair of links 240 provides two orthogonal pivoting axes to the linkage structure.

FIG. 6 illustrates a linkage embodiment of the sheath 2 in which the sheath links include a hollow central orifice 41 and pivot on spherical ball-joint like ball 46 and cup 47 surfaces for two-axis pivoting. The sheath's rigidizing cable 40 runs outside each sheath 2 link's central orifice 41 allowing the assembled links to form a hollow central lumen 42 that can be occupied by the core 1 structure during cannula advancement as well as by items such as surgical instruments which the sheath lumen 42 can guide to a surgical or diagnostic site. The link's central orifice 41 has a diameter D2 that is substantially similar to diameter D1, described above.

The rigidizing sheath links 45 may include at least two cable-guiding features 44 external to the central lumen 42. The cable 40 and cable-guiding features 44 are configured for low friction sliding. Friction may be further reduced by encasing the cable in a cable housing formed of a material with low-friction properties, such as PTFE, HDPE, and the like, thus separating it from the cable-guiding features 44. Alternatively, the cable-guiding features themselves could be manufactured from low friction materials different from that of the rest of the links. When the links 45 are assembled into a rigidizing structure 46, the cable-guiding features 44 form segmented channels running the length of the rigidizing structure 46. Since the cables 40 do not run down the central axis of the sheath 2, cables running on opposite sides of the sheath 2 must effectively change length when the sheath 2 bends. Cable segments closer to the center of curvature relative to the structure's neutral axis will have to shorten. Likewise, cable segments further from the center of curvature relative to the sheath's 2 neutral axis will have to lengthen.

Figure 7:
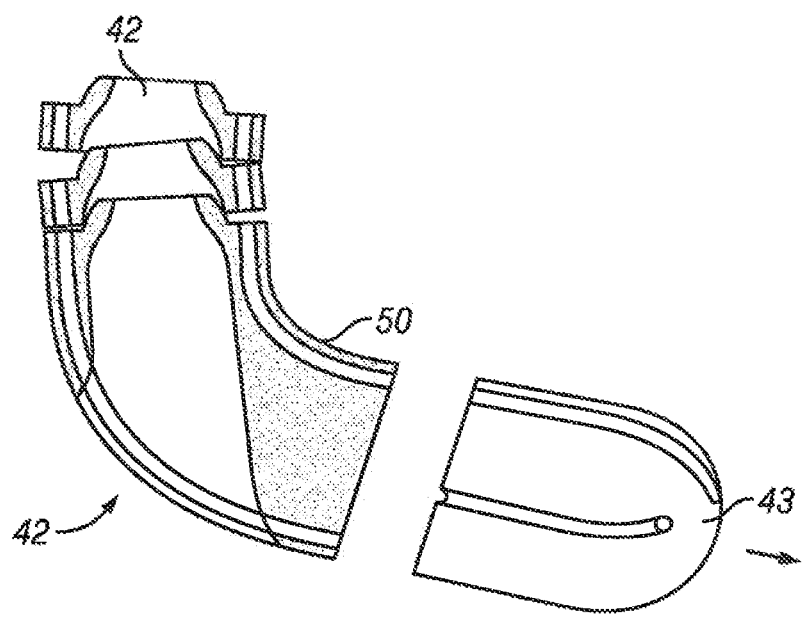
FIG. 7 is a sectional view of an off-axis tensioning mechanism for a cable-rigidized sheath linkage.

An embodiment of a linkage sheath with two cable-guiding channels an equal radial distance from the sheath's central axis may employ the single cable 40 wrapping around a pulley 43, which may be a rotating component, sliding surface, or the like, to run back and forth along the length of both cable-guiding channels. As the structure bends, the inner cable path will shorten the same amount as the outer cable path lengthens and cable length will move from the shortening side around the pulley 43 to the lengthening side. Tension on the pulley 43 with respect to the linkage structure 46 tightens the entire cable 40 and stiffens the sheath 2 by increasing friction between the links. Referring to FIG. 7, the sheath's tensioning pulley 43 may be positioned off-axis such that the sheath central lumen 42 is clear and able to receive the core 1 or surgical instruments. A cable-guiding element 50 at the base of the sheath 2 acts to redirect the tensioning cable 40 to an off-axis pulley 43 and away from the sheath's central lumen 42.

Figure 8:
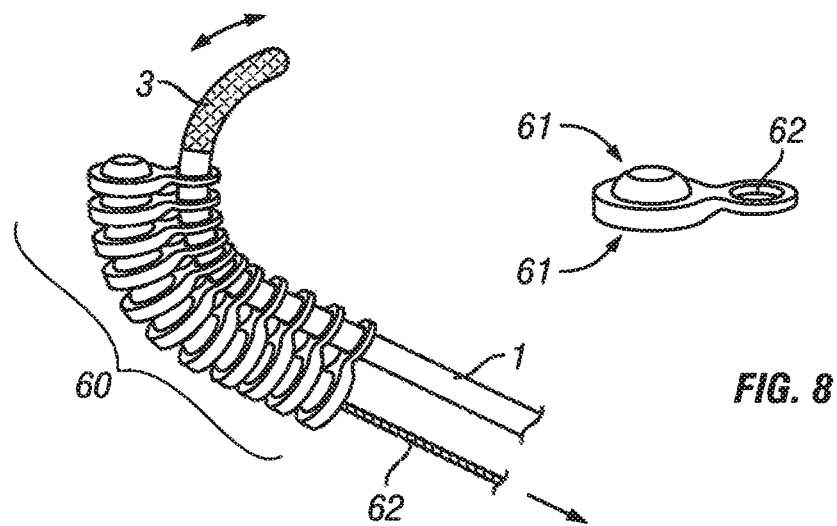
FIG. 8 is a perspective view of an alternate embodiment of a laterally parallel sheath linkage.

Referring to FIG. 8, the sheath rigidizing linkage structure 60 may run parallel to the core 1 without being coaxial with it. Each link may include dedicated rigidizing features 61 through which a rigidizing cable 62 may run and at least one lateral orifice 62 which, when multiply assembled in the complete linkage, form a laterally parallel segmented lumen through which the core 1 or surgical tools may run. The lateral orifice 62 has a diameter D3, which is substantially similar to diameter D1, described above.

Figure 9:
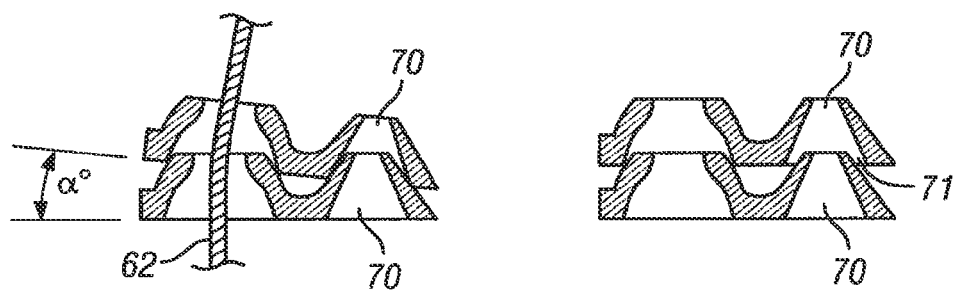
FIG. 9 is a sectional view of a laterally parallel sheath linkage.

FIG. 9 depicts a laterally parallel sheath linkage. The laterally parallel sheath 60a may form a lateral lumen 70 capable of forming varying radii of curvature by nesting conical shapes that form the lateral lumen 70, leaving sufficient mechanical clearance 71 to accommodate an angle α between adjacent links. The angle α is preferably in the range from about zero degrees to about 90 degrees. The lateral lumen diameter D4 is substantially similar to diameter D1, described above.

Figure 10:
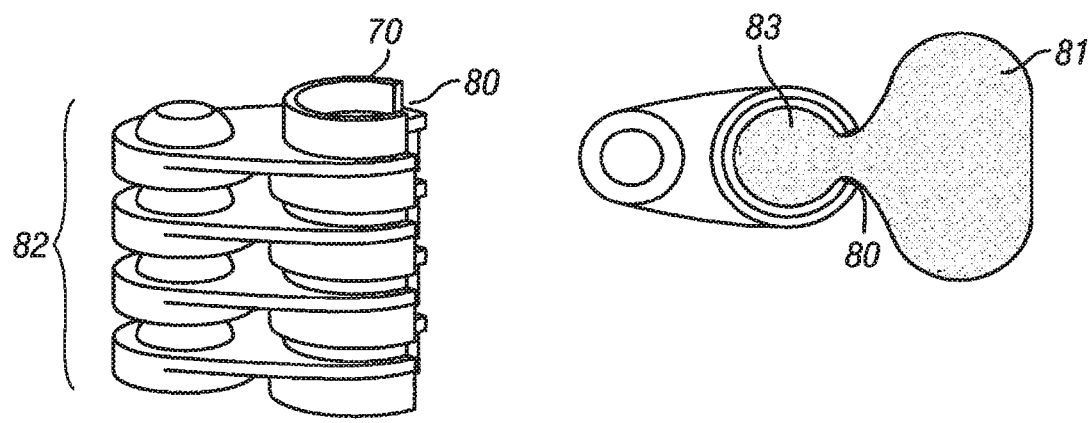
FIG. 10. shows perspective and end views of an open-sided sheath linkage.

FIG. 10 depicts an alternate embodiment of a linkage. Linkage 82 with the parallel lateral lumen 70 may include an open side 80 such that objects 81 larger than the lumen diameter D4 may be introduced to and withdrawn from the surgical or diagnostic site using the combinations of the open sides 80 to retain therein a matching portion 83 on the object 81.

Figure 11:
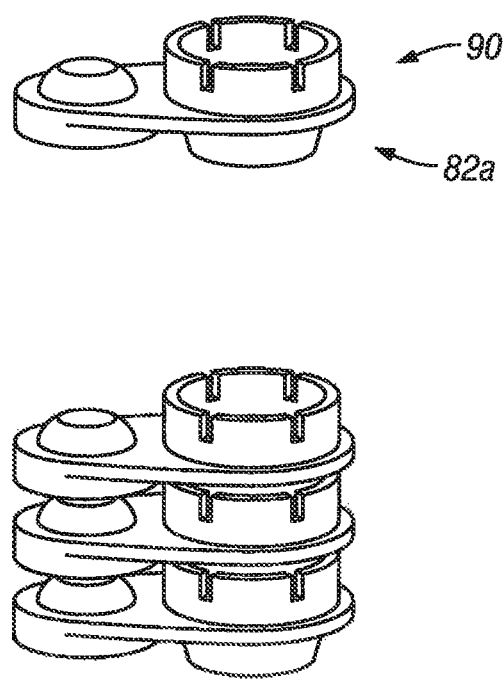
FIG. 11 is a perspective view of a laterally parallel sheath linkage with compliant elements.

FIG. 11 depicts another alternate embodiment of a linkage. Linkage 82a with the parallel lateral lumen 70 may employ flexible elements 90 in the lumen portion of each link that partially overlap each adjacent link. The flexible elements serve to form a smoother and larger segmented lumen than would be formed by purely rigid links by flexing when formed into a radius rather than requiring clearance for the entire range of motion between the links.

Figure 12A:
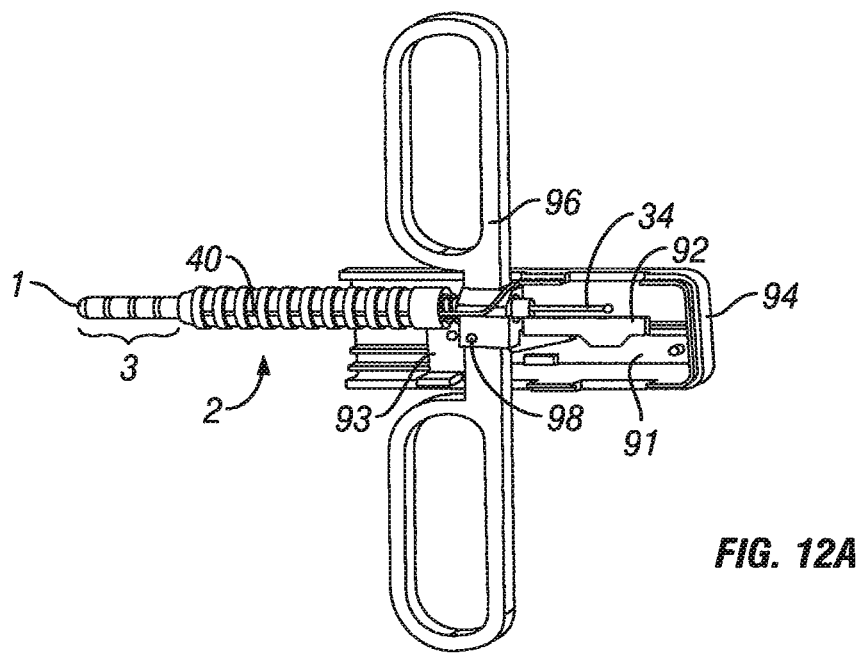
FIGS. 12A-12H illustrate various views of an alternating advancement mechanism in accordance with the present invention.
Figure 12B:
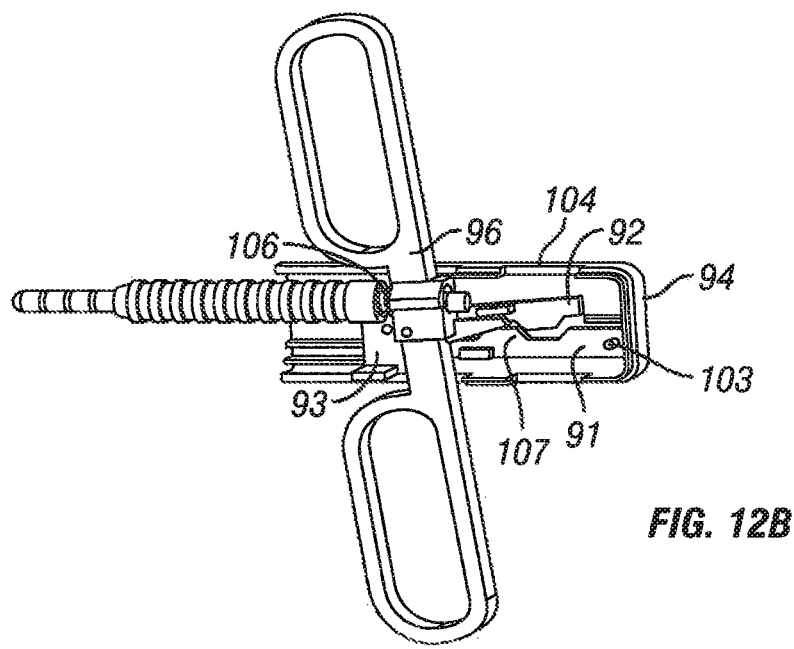
Figure 12C:
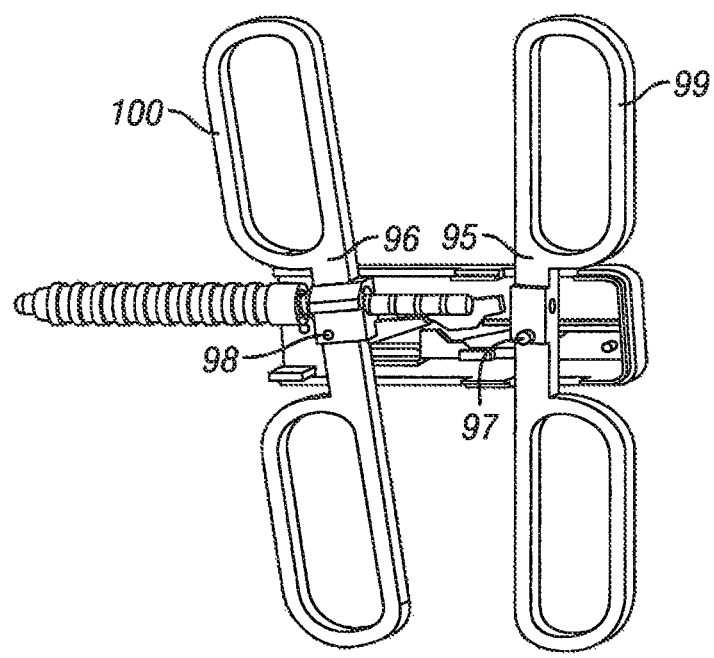
Figure 12D:
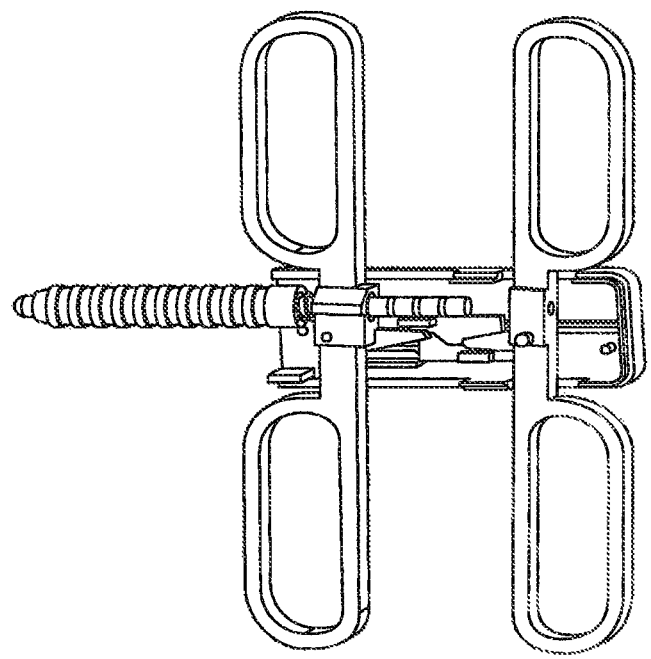
Figure 12E:
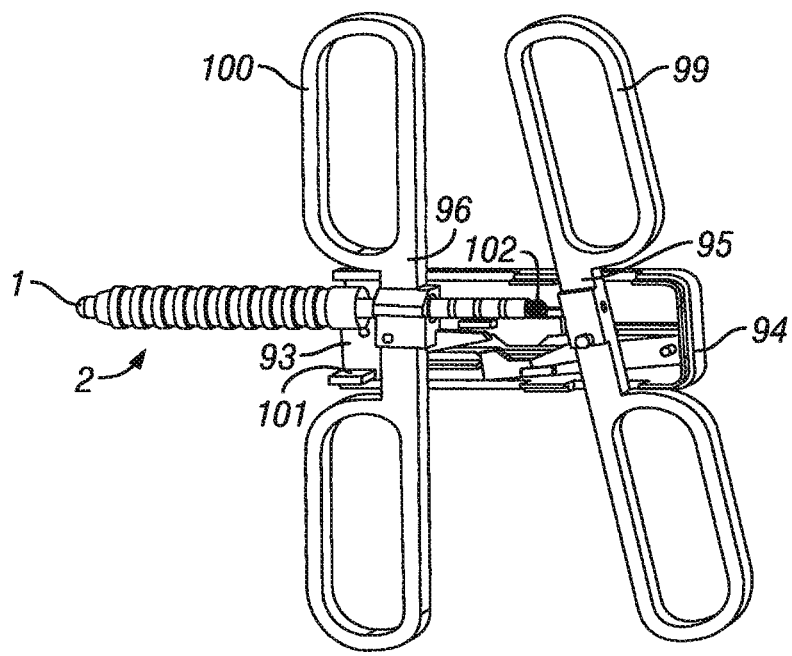
Figure 12F:
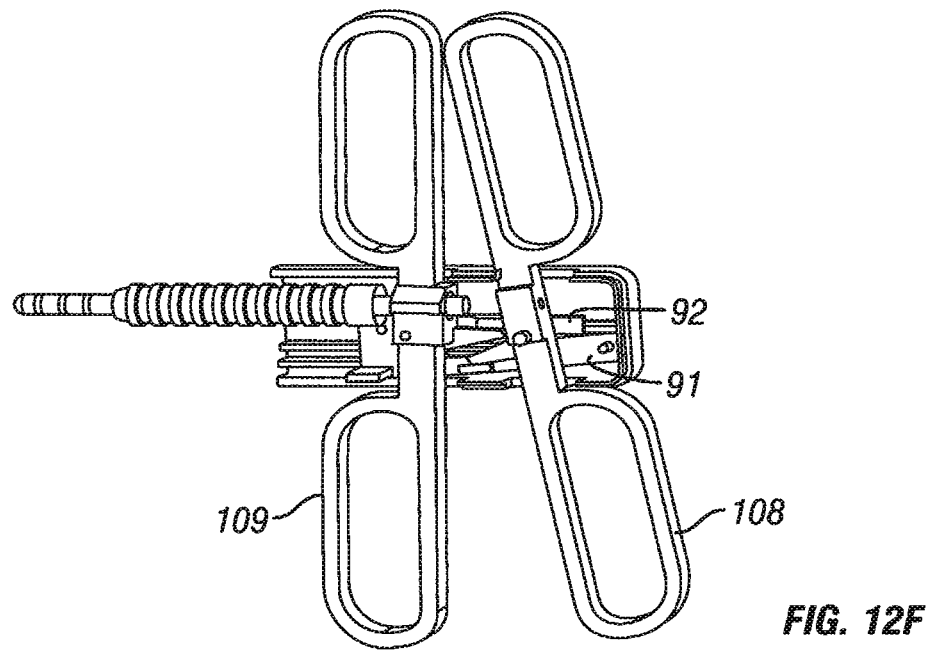
Figure 12G:
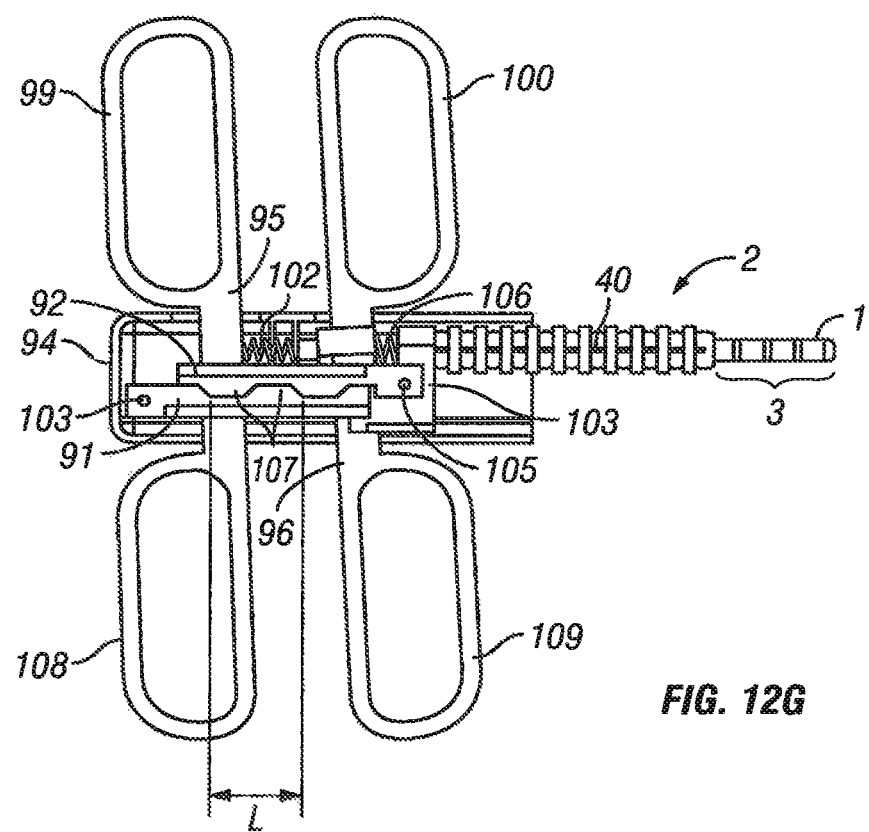
Figure 12H:
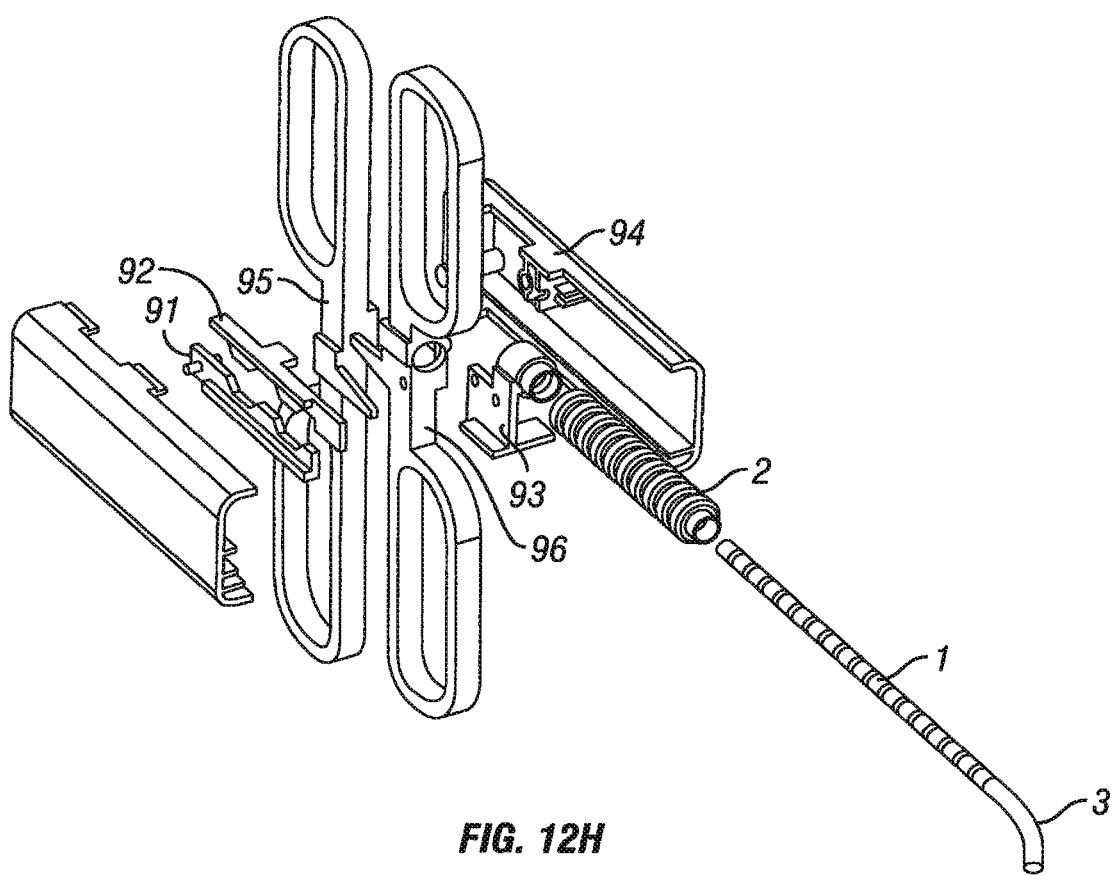

Referring to FIGS. 12A-12G, a mechanism for advancing parallel rigidizing elements may include two opposing racks 91 and 92 that alternatingly advance relative to each other. Referring to FIG. 12G, the maximum amount of incremental advancement, length 'L', is ideally limited to the length of cannula having the steerable tip 3. A linearly sliding shuttle 93 supports one rack and a housing 94 supports the other rack. The core actuation handle 95 (not shown for clarity in FIG. 12A and FIG. 12B) and core rack 91 are each pivotally attached to the housing 94. The sheath actuation handle 96 and sheath rack 92 are each pivotally attached to the shuttle 93. The core and sheath actuation handles 95 and 96 are attached to the rigidizing cables 40 and 34 of the sheath 2 and core 1, respectively. Upon actuation by the user, these handles rotate on their pivots 97 and 98 to first relax their respective rigidizing structure, disengage their respective rack from the other, which remains temporarily fixed, and transmit the force which slides the housing 94 and shuttle 93 with respect to one another to advance the shape-transferring cannula.

Beginning the advancement sequence as shown in FIG. 12B, spreading the handholds 99 and 100 (core advancement handhold 100 not shown for clarity) apart biases the core handle 95 (not shown for clarity) against it's mechanical stop 104 in the housing 94 and rotates the sheath handle 96 on its pivot 98, first compressing the sheath rigidizing spring 106, relaxing the sheath linkage 2, and then disengaging the sheath rack 92 from the currently-fixed core rack 91. The sheath rack 92 disengages the core rack 91 by rotating on its pivot 105 against the force of the sheath rack bias spring 113. The sheath rack 92 is rotated away from the core rack 91 by the force of the sheath rack lifter 115, which extends from the sheath handle 96, acting against the rack's lift tab 117. An initial gap between the sheath rack lifter 115 and rack's lift tab 117 allows the sheath handle 96 to rotate enough to compress the sheath rigidizing spring 106 and relax the sheath 2 before the sheath rack 92 is disengaged from the core rack 91. As illustrated in FIG. 12C, continued spreading of the actuation handles 95 and 96, with racks 91 and 92 disengaged, translates the handles apart from each other and advances the shuttle 93 and sheath 2 relative to the housing 94 and core 1.

As illustrated in FIG. 12D, releasing the handle spreading pressure allows the sheath rigidizing spring 106 to rotate the sheath handle 96 back to its resting position and re-stiffen the sheath 2 by tensioning the sheath rigidizing cable 40. The rotation of the sheath handle 96, in turn, rotates the sheath rack lifter 115 away from the sheath rack 92, allowing the sheath rack bias spring 113 to rotate the sheath rack 92 towards the core rack 91. Re-engagement of the racks locks the mechanism in a sheath-forward position shown in FIG. 12D.

Continuing the advancement sequence as shown in FIG. 12E, squeezing the advancement handholds 99 and 100 of the actuation handles 95 and 96 such that they rotate towards each other biases the sheath handle 96 solidly against it's mechanical stop 101 on the shuttle 93 and rotates the core handle 95 on its pivot 97, first compressing the core rigidizing spring 102, relaxing the core linkage 1, and then disengaging the core rack 91 from the currently-fixed sheath rack 92. The core rack 91 disengages the sheath rack 92 by rotating on its pivot 103 against the force of the core rack bias spring 112. The core rack 91 is rotated away from the sheath rack 92 by the force of the core rack lifter 114, which extends from the core handle 95, acting against the rack's lift tab 116. An initial gap between the lifter 114 and lift tab 116 allows the core handle 95 to rotate enough to compress the core rigidizing spring 102 and relax the core 1 before the core rack 91 is disengaged from the sheath rack 92. The racks 91 and 92 being disengaged from each other, continued squeezing as shown in FIG. 12F translates the handles 95 and 96 closer together by advancing the housing 94 and core 1 relative to the shuttle 95 and sheath 2.

Releasing the squeezing pressure on the advancement handholds 99 and 100 allows the core rigidizing spring 102 to rotate the core handle 95 back to its resting position and re-stiffen the core 1 by tensioning the core rigidizing cable 34. The rotation of the core handle, in turn, rotates the core rack lifter 114 away from the core rack 91 allowing the core rack bias spring 112 to rotate the core rack 91 towards the sheath rack 92. Re-engagement of the racks locks the mechanism in the sheath-back position shown on FIG. 12A.

Referring to FIG. 12G, the difference in engaged length of the racks 91 and 92 between the sheath-back position and the sheath-forward position, length as well as the position of the sliding stop structures 110 and 111 in the housing 94 and shuttle 93 define the maximum relative motion for incremental advancement between the sheath 2 and core 1 elements. The amount of incremental advancement, length is preferably limited to the length of the steerable tip 3. Rack features 107 such as teeth define the increments in which the shape-transferring cannula may be mechanically advanced or retracted. The rack features 107 may be configured to allow only integral advancement of units the length of the entire steerable tip 3 as shown in FIG. 12O or, alternatively, may be configured allow units of advancement fractions of that length.

The rack mechanism described above may also withdraw the shape-transferring cannula in controlled increments through a process reversing the advancement sequence. Withdrawal of hand-holds 108 and 109 on the ends of the handles 95 and 96 opposite the advancement ends actuate the mechanism in reverse using the same gripping and spreading finger/thumb motions used to advance the cannula.

Figure 20A:
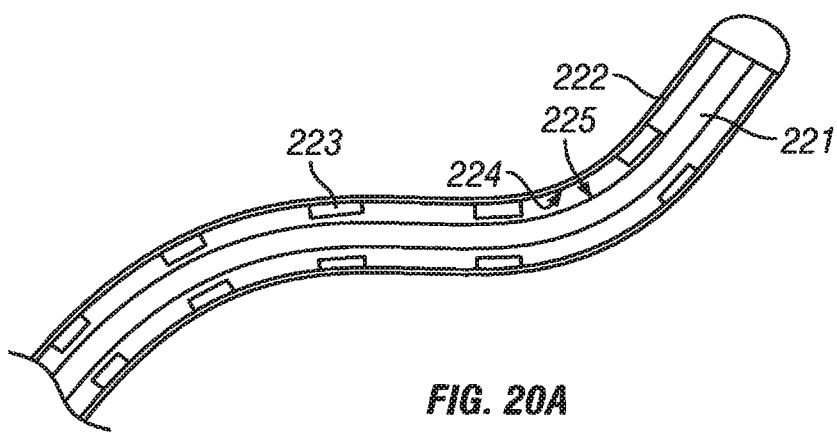
FIGS. 20A and 20A illustrate sectional views of a cannula structure including active material elements.

In another embodiment of the invention, FIG. 22 depicts rigidizing structures including inner and outer concentric tubes, 221 and 222 respectively, separated by short segments of materials 223 that change shape when energized, such as electroactive polymer (EAP), which changes shape when exposed to electric fields. The inner tube 221 may or may not have an open lumen. When employing biaxially active materials such as EAP, the active material components are oriented to contract longitudinally and expand radially when energized. The active material components may be employed in a normally-non-interfering configuration or a normally-interfering configuration. In a normally-non-interfering configuration the active material components 223 are each attached to one of the concentric tubes 221 or 222 such that they do not contact the other tube, as shown in FIG. 20a, when not energized. When energized, the radial expansion of the active material components 223 causes mechanical interference with the other tube, as in FIG. 20b, thus preventing motion between the opposed surfaces 224 and 225 and effectively locking-in the curvature of the rigidizing structure. According to the present invention, one may substitute materials that change shape when exposed to electric current, magnetic fields, light, or other energy sources. The same rigidizing effect may be achieved by replacing normally-non-interfering active material components 223 with non-interfering balloons expandable by gas or liquid fluid pressure. Alternately, such materials may be placed in a normally-interfering configuration between concentric tubes 221 and 222 such that they interfere, as in FIG. 20b when not energized and contract radially to the state depicted in FIG. 20a when energized. For example, a normally-rigid structure made stiff by normally-interfering EAP components 223 may be made flexible by applying a voltage to the EAP components such that they contract radially to the non-interfering state depicted in FIG. 20a, relieving the mechanical interference and allowing relative motion between the opposed surfaces 224 and 225 of the concentric tubes 221 and 222. Similarly, normally-interfering balloons replacing normally-interfering active material components 223 may be collapsed by applying a relative vacuum.

Referring to FIG. 13A, in an alternate embodiment of the invention, the rigidizing sheath 2 can include rotating wedge links 130. The wedge links 130 have hollow central axes 131 that form the sheath's lumen 42 as well as two interface features 132 angled with respect to one another. For example, the angle between the links can be between about zero degrees and about 90 degrees. The perpendicular centerlines 133 of the interface surfaces define axes of rotation between the links. As depicted diagrammatically in FIGS. 13B and 13C, the wedge links 130 in a sample starting position in FIG. 13B rotate with respect to neighboring links 134 at the connecting interface 132 between links. This rotation forms curves as shown in FIG. 13C in the sheath 2 structure while maintaining a substantially constant sheath lumen 42 volume. Impeding rotation between links rigidizes the structure. Link rotation can be prevented through any of the ways described above for impeding relative motion between links. The wedge links 130 may be formed as sections of spheres as shown in FIG. 13A to avoid creating sharp corners when curves are formed, leaving a relatively smooth and atraumatic outer surface.

Figure 14A:
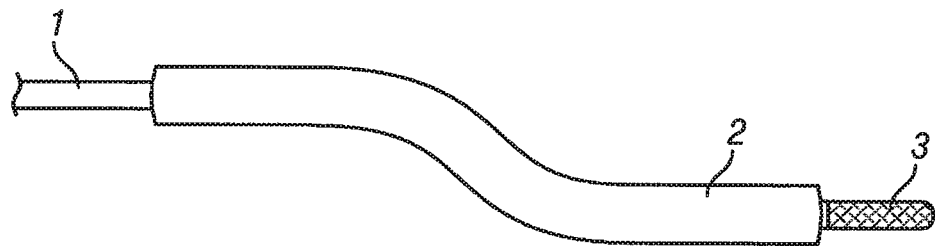
FIGS. 14A-14C is a diagrammatic view of a cannula structure including a passive element.
Figure 14B:
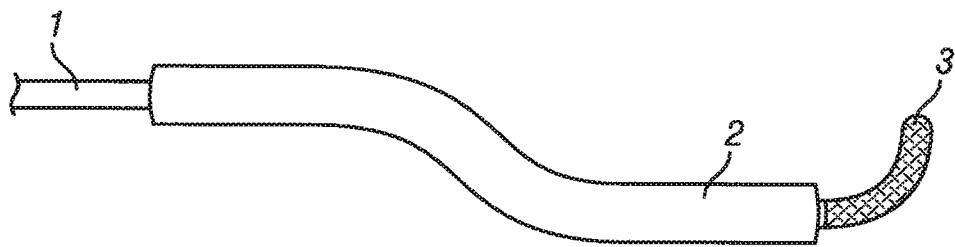
Figure 14C:
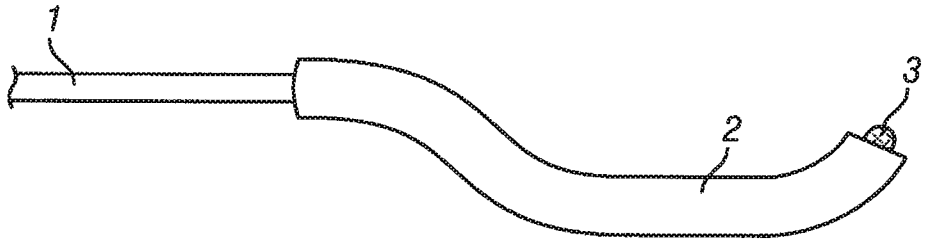

FIGS. 14A-14C depict another embodiment of the invention in which one of the two parallel elements in the shape-transferring cannula is passive. The passive element is more rigid than the relaxed rigidizing structure and more flexible than the stiffened rigidizing structure. The passive element is less mechanically complex than an equivalent rigidizing structure, not requiring rigidizing cables 34 and 40 or other mechanisms to serve the shape-transfer function. Thus a shaped cannula assembly with a passive sheath may be narrower in cross-section than an assembly formed of two rigidizing structures. In FIG. 14A the core 1 is relaxed such that it is more flexible than the sheath 2 and has been advanced such that the steerable tip 3 protrudes ahead of the sheath 2. In FIG. 14B the core 1 is stiffened such that it is more rigid than the sheath 2 and the user deflects the steerable tip 3 towards the direction of intended cannula advancement. In FIG. 14C the core 1 remains stiffened such that it is more rigid than the sheath 2 and the sheath is then advanced over the core and its steerable tip 3. The sheath 2 assumes the core's longitudinal shape including the new bend introduced by the user through the deflected steerable tip 3. Elements of a passive link structure could be mechanically energized to encourage them to move relative to one another when being advanced past a relatively rigid structure. Mechanical energizing can be achieved by vibrating the passive structure with any suitable device, such as a piezoelectric transducer, voicecoil, or eccentrically weighted motor.

Embodiments of the invention that employ continuous, non-segmented, parallel core and sheath structures can be made smaller in cross-section than mechanically-stiffened linkage structures. Such structures may be constructed such that they become relatively rigid when energized or become relatively flexible when energized.

Figure 15:
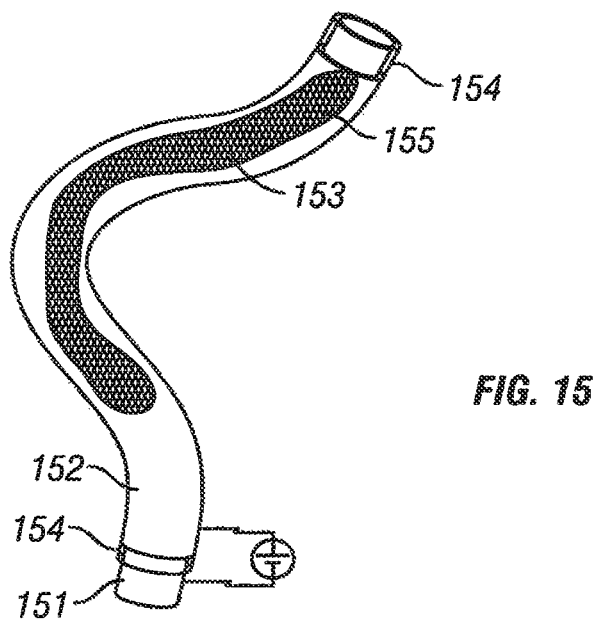
FIG. 15 is a sectional view of a continuous stiffening cannula structure.

FIG. 15 depicts a continuous, parallel shape-transferring core and sheath structure. The core 1 and sheath 2 structures can each include inner 151 and outer 152 flexible tubes containing stiffening material 153 that increases in viscosity or otherwise stiffens when energized. Examples of such substances are electrorheological fluid, which stiffens upon exposure to electrical potential, and magnetorheological fluid, which stiffens upon exposure to magnetic fields. A rigidizing structure configured as a core or as a sheath may be built-up of inner 151 and outer 152 containment tubes with stiffening material 153 sandwiched in between. In the case of a core, the inner tube may be a solid element such as plastic monofilament, lacking a lumen. In the case of a structure employing electrorheological fluid, flexible electrical contacts may line the length of each containment tube or the tube itself may be made of electrically-conductive plastic or other similar material. A section of electrically insulating material 154 may connect the tubes 151 and 152 at their proximal and distal ends, mechanically connecting the tubes 151 and 152 and sealing the electrorheological fluid within. A woven mesh or other similar separating material 155 sandwiched with the electrorheological fluid between the tubes 151 and 152 may act as a baffle, restricting the flow of viscous fluid so as to increase the rigidity of the structure when energized, and as an insulator when an electrical potential is used to energize the elements. The tubes 151 and 152 themselves may contain baffling features such as grooves or threads and may also contain a layer of insulating material, obviating the need for a separating material 155. A similar structure employing magnetorheological fluid could be constructed with at least one containment tube containing electrical conductors arranged in such a manner as to generate a magnetic field sufficient to rigidize the structure.

Figure 16:
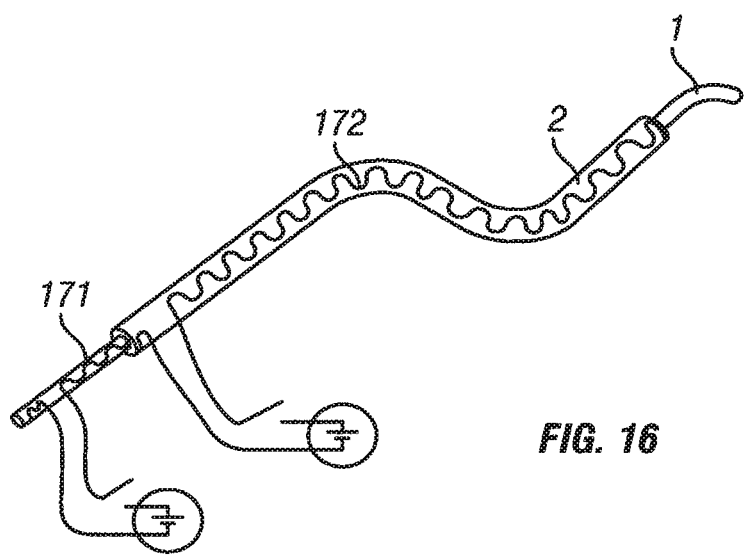
FIG. 16 is a perspective view of a cannula structure formed with normally-rigid, thermally relaxing materials.
Figure 23:
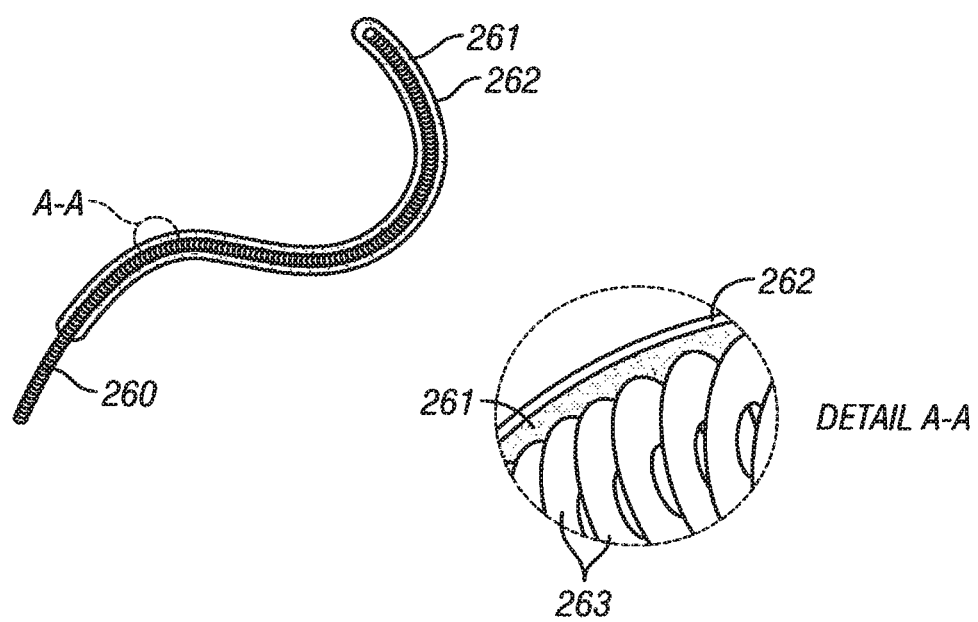
FIG. 23 depicts a thermally relaxing normally-rigid structure.

A shape-transferring cannula structure may be constructed of normally-rigid core 1 and sheath 2 elements which, in proper sequence, become flexible when energized and re-stiffen when they return to an un-energized state. Each element can become flexible enough, when energized, to be advanced along a relatively rigid mating structure and then, when de-energized, become rigid enough to mechanically support the advancement of an energized parallel structure. Referring to FIG. 16, parallel normally-rigid core 1 and sheath 2 elements may include in their construction thermoplastic, thermoplastic alloys such as Kydex™ (acrylic-PVC alloy), urethane alloys, or similar materials that soften to a flexible state when heated above a transition temperature by embedded heating elements 171 and 172 or any suitable mechanism. The transition temperature can be selected through design and material composition to be somewhat higher than normal body temperatures. The normally-rigid parallel structures may contain heating elements that momentarily increase their temperatures above the flexibility transition temperature. Surrounding body fluid such as blood, saline solution, or lymph can serve as a heat sink to quickly draw heat away and re-stiffen the structures when the momentary heating is ceased. Similarly, as shown in FIG. 23, normally-rigid core 1 or sheath 2 structure can include a guidewire 260 with wirewound coils in its construction. The coils 263 can be at least partially potted in a low-temperature flowing material 261 such as wax or polymer which adheres to the coils. The low-temperature flowing material 261 may be contained within a compliant cover 262. In an un-energized state the flowing material 261 is relatively solid and prevents the coils 263 from moving substantially with respect to one another, thus substantially locking-in the curvature of the structure. When energized through heating, the flowing material 261 softens sufficiently to allow relative motion between coils 263, thus relaxing the structure.

Figure 19A:
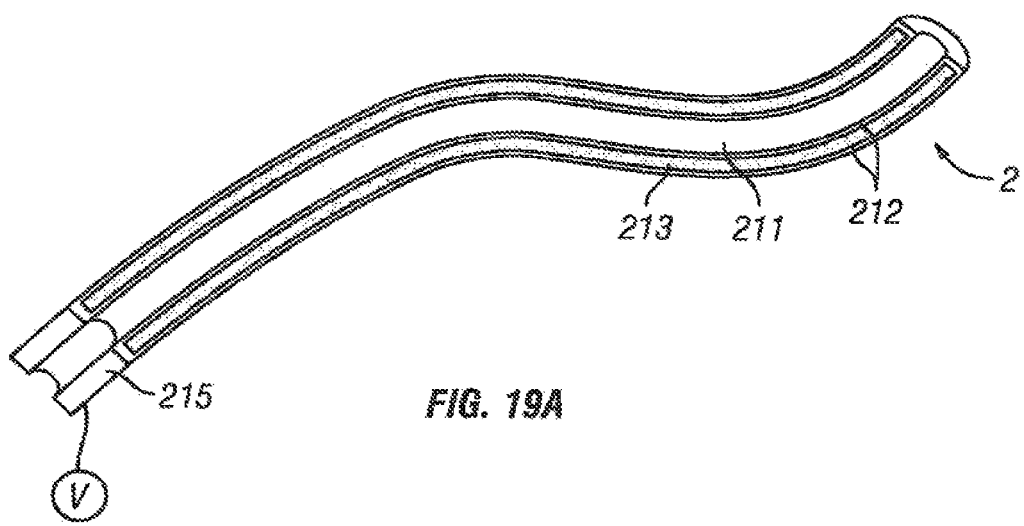
FIGS. 19A and 19B show a sectional view of normally-rigid, vibrationally relaxing cannula structure elements.
Figure 19B:
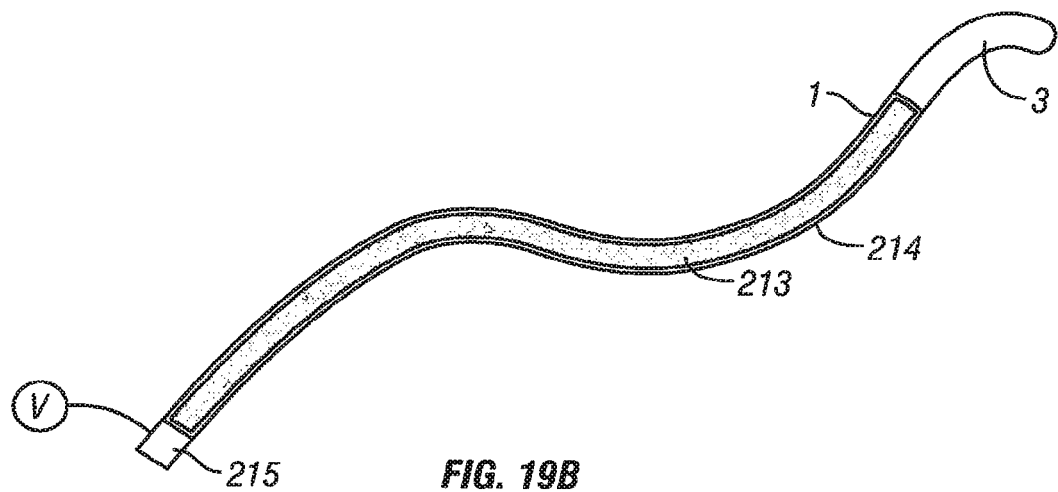

Referring to FIGS. 19A and 19B, shape-transferring cannula can be built of normally-rigid core 1 and sheath 2 structures, each including flexible tubes 212 and 214 respectively, containing substantially stiff materials 213 that relax upon vibration. Such materials can include interlocking particles like sand grains or normally-viscous fluid, such as xanthan gum that becomes less viscous upon agitation. Vibrating each structure, for example with a vibrating element 215 such as a piezoelectric transducer, a voicecoil, or a motor with an eccentrically mounted weight, could temporarily relax it to a flexible state by loosening the interlocking particles or by causing the contained fluid to transition to a less viscous state. Alternatively, the containment tubes 212 and 214 themselves could be constructed of or contain a piezoelectric material such as PVDF (polyvinylidene fluoride) along their length such that each entire tube could actively vibrate when energized with an alternating voltage V.

Figure 20B:
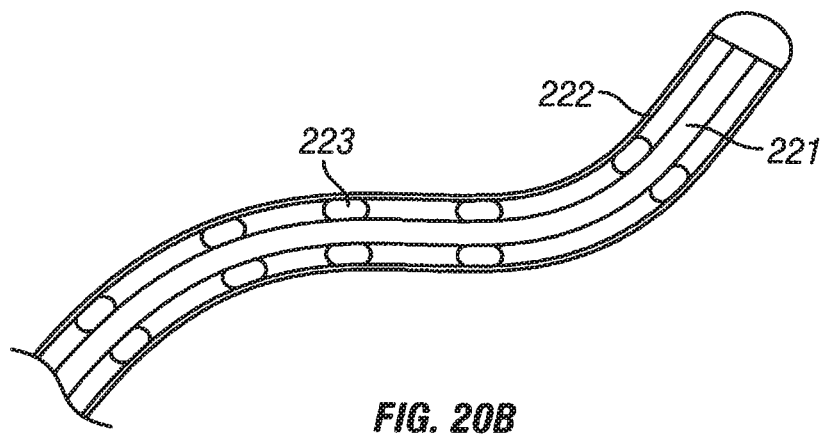

In another embodiment of the invention, FIG. 22 depicts rigidizing structures including inner and outer concentric tubes, 221 and 222 respectively, separated by short segments of materials 223 that change shape when energized such as electroactive polymer (EAP), which changes shape when exposed to electric fields. The inner tube 221 may or may not have an open lumen. When employing biaxially active materials such as EAP, the active material components are oriented to contract longitudinally and expand radially when energized. The active material components may be employed in a normally-non-interfering configuration or a normally-interfering configuration. In a normally-non-interfering configuration, the active material components 223 are each attached to one of the concentric tubes 221 or 222 such that they do not contact the other tube, as shown in FIG. 20A, when not energized. When energized, the radial expansion of the active material components 223 causes mechanical interference with the other tube, as illustrated in FIG. 20B, thus inhibiting or preventing motion between the opposed surfaces 224 and 225 and effectively locking-in the curvature of the rigidizing structure. The same invention may substitute materials that change shape when exposed to electric current, magnetic fields, light, or other energy sources. The same rigidizing effect may be achieved by replacing normally-non-interfering active material components 223 with non-interfering balloons expandable by gas or liquid fluid pressure. Alternately, such materials may be placed in a normally-interfering configuration between concentric tubes 221 and 222 such that they interfere, as in FIG. 20B when not energized and contract radially to the state depicted in FIG. 20A, when energized. For example, a normally-rigid structure made stiff by normally-interfering EAP components 223 may be made flexible by applying a voltage to the EAP components such that they contract radially to the non-interfering state depicted in FIG. 20A, relieving the mechanical interference and allowing relative motion between the opposed surfaces 224 and 225 of the concentric tubes 221 and 222. Similarly, normally-interfering balloons replacing normally-interfering active material components 223 may be collapsed by applying a relative vacuum.

Figure 17A:
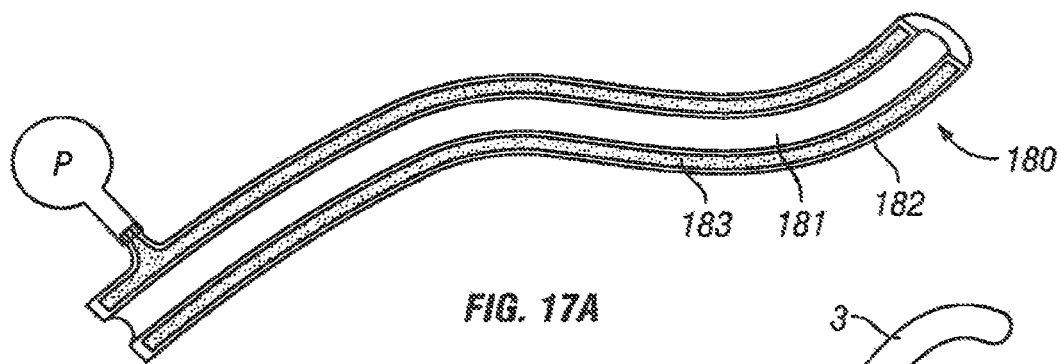
FIGS. 17A and 17B illustrate sectional views of vacuum-stiffening cannula structure elements.
Figure 17B:
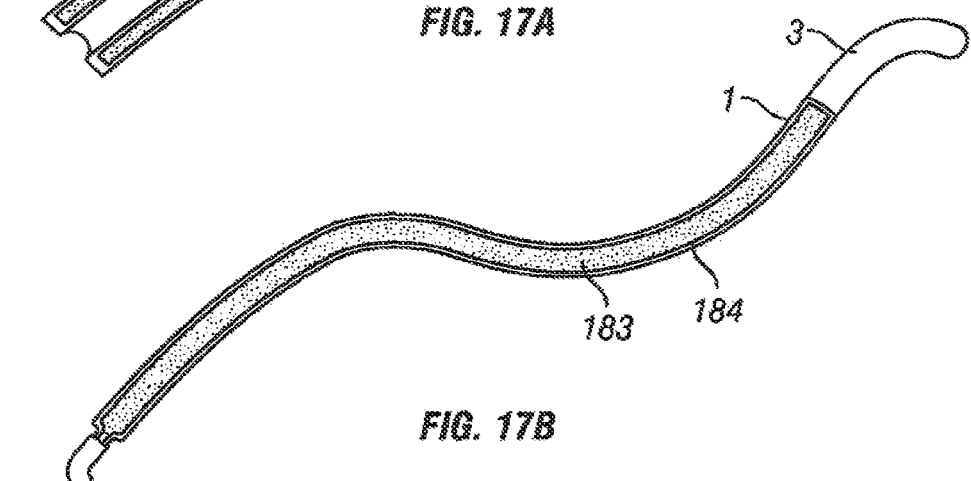

Referring to FIG. 17A, core and sheath rigidizing 180 structures can include compliant inner and outer tubes, 181 and 182, containing compression-stiffening particles 183 in the annular space between the opposing tube surfaces. The compression stiffening particles 183 are made of materials such as expanded polystyrene that interlock and form a substantially rigid structure when compressed. Such compression can occur when the space containing the compression-stiffening particles is placed under a relative vacuum P. Alternatively, external pressure may be applied to the material in the annular inter-tubal space to compress and stiffen it. For example, pressure may be applied to the internal concentric tube such that it expands and presses compression-stiffening material in the inter-tube space against the external concentric tube. Referring to FIG. 17B, core 1 structure can include a compliant tube 184 containing compression-stiffening particles 183. The structure may be stiffened by putting the tubes interior under relative vacuum P.

Figure 18:
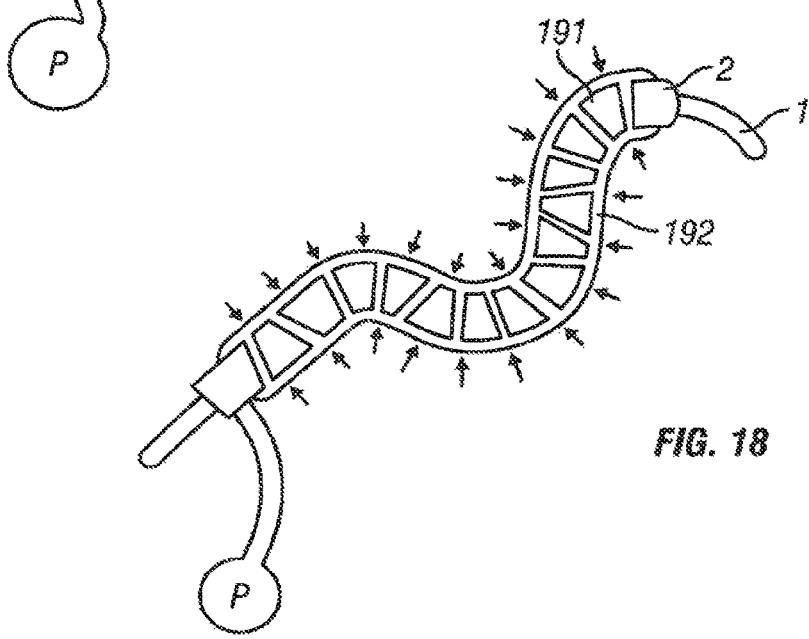
FIG. 18 is a sectional view of a pressure-stiffening cannula structure.

Referring to FIG. 18, a core 1 or sheath 2 structure including links 191 may be rigidized or relaxed via pressure P which can be either positive pressure or relative vacuum. In a normally-rigid configuration, a compliant cover 192 the length of the structure can be stretched taut against the movable links 191 in an equalized pressure environment. The tight covering 192 keeps the links from moving substantially relative to one another, making the rigidizing structure stiff. Application of pressure P underneath the compliant cover 192 expands the cover, allowing the links 191 to rotate relative to one another thereby relaxing the structure. Alternately, in a normally-flexible structure, the compliant cover 192 can loosely cover the links 191 in an equalized pressure environment such that the links can rotate relative to one another. Applying a relative vacuum P inside the compliant cover 192 causes it to compress against the movable links 191, preventing their rotation relative to one another thereby stiffening the structure.

The rigidizing structures described above as a paired system may be also employed singly as an alternatingly rigid and compliant support for a steerable catheter such as an endovascular catheter or flexible endoscope. In such cases as depicted in FIG. 21, the rigidized structure provides support for the catheter to round corners without the possibility of looping because the flexible element is advanced only when the supporting structure is rigid. Similarly, the relaxed rigidizing support is advanced only along the length of the catheter, using it as a guidewire.

In another embodiment of the invention, a steerable catheter such as an endovascular catheter or flexible endoscope may be aided in advancing around tight corners through alternating between advancement of two parallel structures, using the relatively rigid steerable bending section at the tip to advance through a tight anatomical turn without looping.

In one embodiment, the sheath is rigidized and the core with an articulating tip is made flexible. The core is advanced and then rigidized. The articulating tip is pointed in the desired direction of path creation. The sheath is relaxed and advanced over the rigid core.

Figure 24:
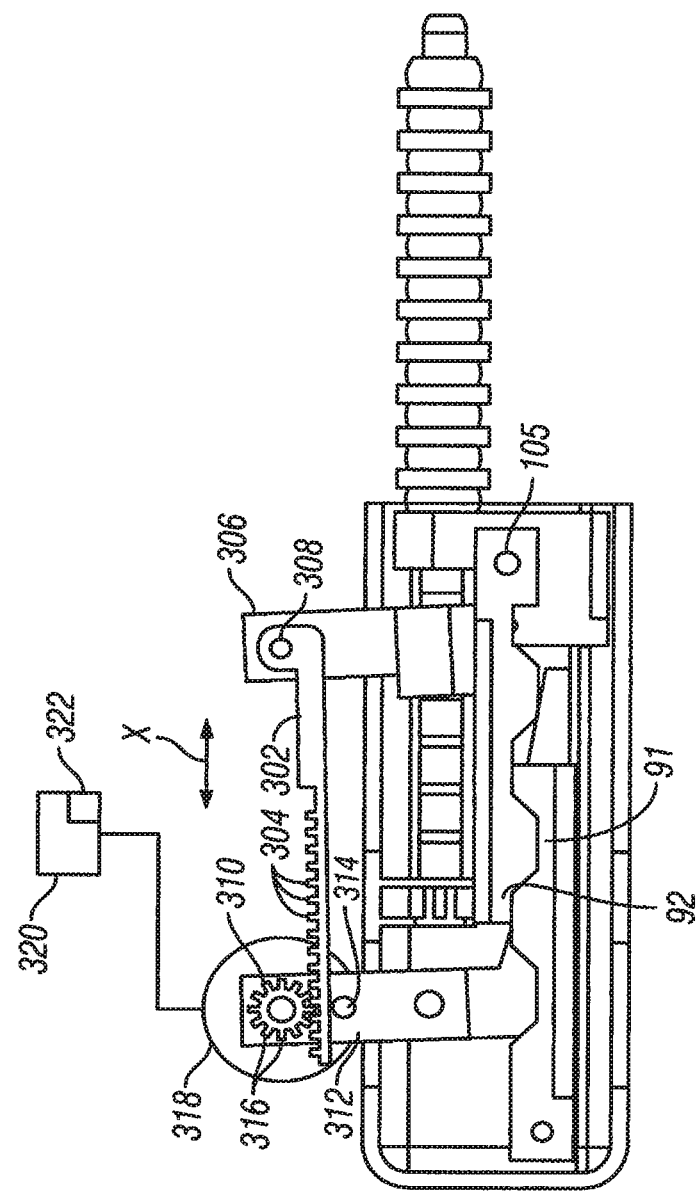
FIG. 24 depicts a motorized advancement mechanism.

Referring now to FIG. 24, yet further aspects of the present invention are illustrated. More specifically, FIG. 24 illustrates that the handholds, such as handholds 99, 100, 108, 109 illustrated in FIGS. 12A-12H, can optionally be replaced with a semi- or fully automated systems, to permit the practitioner's hands to be used for other tasks during the particular procedure performed on a patient. As illustrated in FIG. 24, a rack 302 having teeth 304 is pivotally mounted to the arm 306 at a pivot 308, to which handhold 100 is attached in the embodiment illustrated in FIG. 12G. A pinion 310 having teeth 316, which mate with teeth 304, is rotatably mounted to arm 312, while a pin or the like 314 holds the rack 302 against the pinion. Thus, rotation of pinion 310, such as by a rotary motor 318 or the like, causes arm 306 to move in direction X, while the arm 312 can be separately or simultaneously moved along direction X by pulling or pushing on the arm 312, or the motor 318, with a suitable linear actuator or motor (not illustrated). Further optionally, the activation of the actuators or motors, including motor 318, can be automated by controlling them using an automatic controller 320. By way of example and not of limitation, controller 320 can be a general purpose computer having a memory 322 in which the logic of the sequence of movements of the arms 306, 312 can reside. Alternatively, controller 320 can be a PLC controller or other controller as will be readily appreciated by those of skill in the art, which can automatically control the movements of the arms 306, 312.

Figure 25:
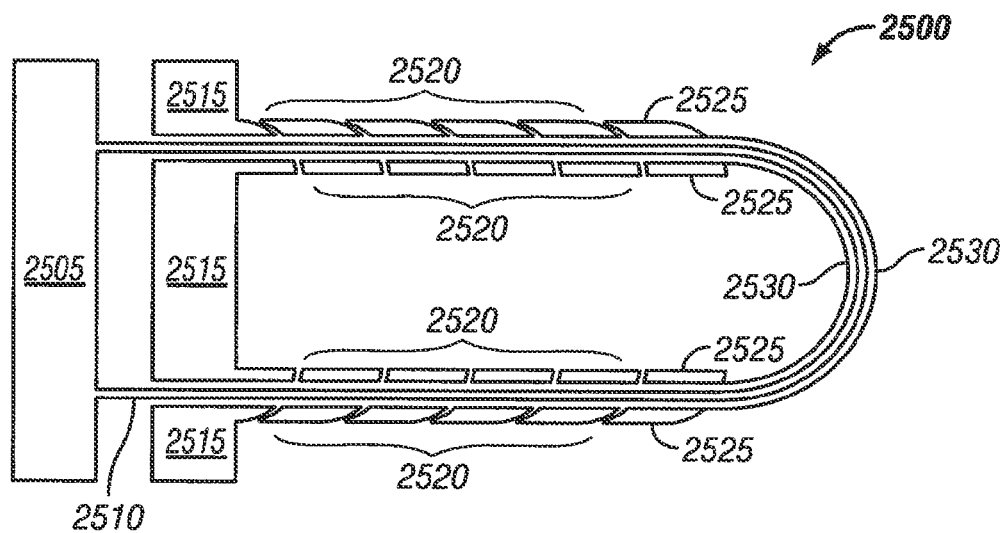
FIG. 25 depicts a rigidizable cannula with distal recirculation.

FIG. 25 shows a cross-sectional view of an embodiment of a cannula system 2500 with a rigidizable structure and distal tensioning-cable recirculation. A static tension anchor 2505 is coupled to a tensioning element 2510. The tensioning element 2510 may be a wire, filament, or multi-stranded cable. The tensioning element may also have a sheath or coating to improve its lubricity (e.g., fluorocarbon polymer). The tensioning element passes through a dynamic tensioning anchor 2515, nested links 2520, terminal link 2525, and a recirculating guide 2530; thus linking them together. The tensioning element 2510 is attached to the static tensioning anchor 2505 at two points, but it is able to slide freely through the dynamic tensioning anchor 2515, nested links 2520, terminal link 2525, and a recirculating guide 2530.

In a preferred mode of operation, the cannula system 2500 is rigidized by holding the static tension anchor 2505 in a fixed position while the dynamic tension anchor 2515 is moved to compress the array of nested links 2520. Since the tensioning element 2510 forms a loop through the recirculating guide 2530, the displacement of the recirculating guide 2530 and the terminal link 2525 is not a function of the compression of the nested links 2520, the rigidization of the cannula system 2500 and the accommodation of the shortening of the cannula system 2500 due to compression is accomplished through the displacement of the dynamic tension anchor 2515.

The distal recirculating guide 2530 will have a displacement that is governed primarily by the pretension slack and stretching of the tensioning element 2510. For a cannula system having nested links 2520 that are fabricated from material (e.g., organic polymer) with a low elastic modulus, the distal displacement is considerably smaller in magnitude than the change in length of the cannula system when rigidized. Also, the distal recirculating architecture increases the effective flexibility of the distal linkage by minimizing the length of cable that must be slid through the cable channels when the distal linkage is put into a turn (e.g., by being slid over an endoscope steering tip).

Figure 26:
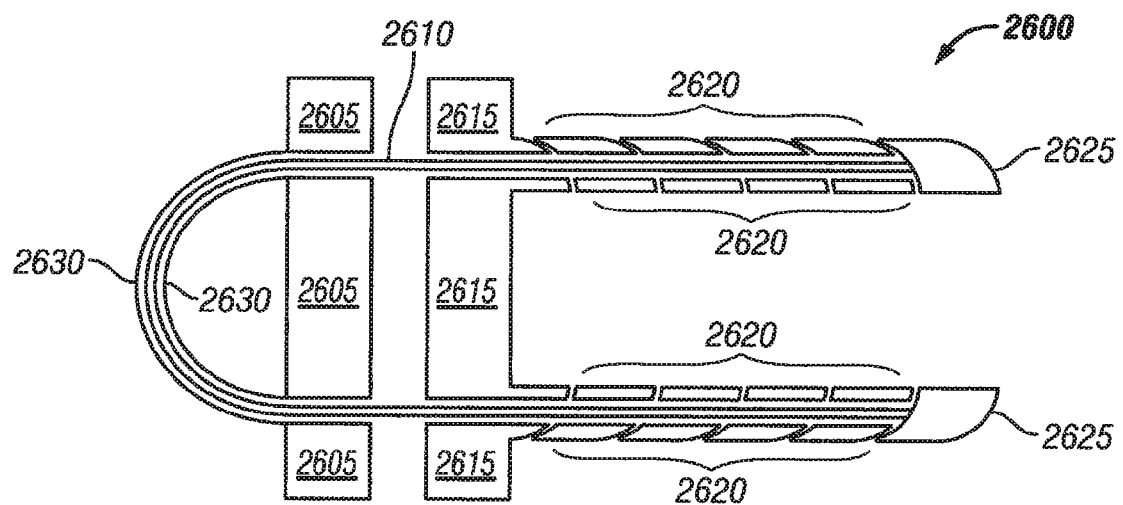
FIG. 26 depicts a rigidizable cannula with proximal recirculation.

FIG. 26 shows a cross-sectional view of an embodiment of a cannula system 2600 with a rigidizable structure and proximal recirculation. A static tension anchor 2605 is coupled to a proximal recirculation guide 2630 that houses a tensioning element 2610. The tensioning element 2610 may be a wire, filament, or multi-stranded cable. The tensioning element may also have a sheath or coating to improve its lubricity. The tensioning element passes through a dynamic tensioning anchor 2615, nested links 2620, and is attached to terminal link 2625; thus linking them together. The tensioning element 2610 is attached to the terminal link 2625 at two points, but it is able to slide freely through the dynamic tensioning anchor 2615, nested links 2620, and proximal recirculating guide 2630.

In a preferred mode of operation, the cannula system 2600 is rigidized in a manner similar to that described for the cannula system 2500. The static tension anchor 2605 is held in a fixed position while the dynamic tension anchor 2615 is moved to compress the array of nested links 2620. Displacement of the distal end (terminal link 2625) is governed primarily by the elasticity and slack of the tensioning element 2610, whereas the shortening of the cannula system due to interlink gap closure and link deformation is accommodated by the displacement of the dynamic tension anchor 2615. This configuration creates a more flexible proximal section as the least length of tensioning wire is required to circulate for a proximal bend (whereas the entire wire would have to recirculate for a distal bend).

Figure 27:
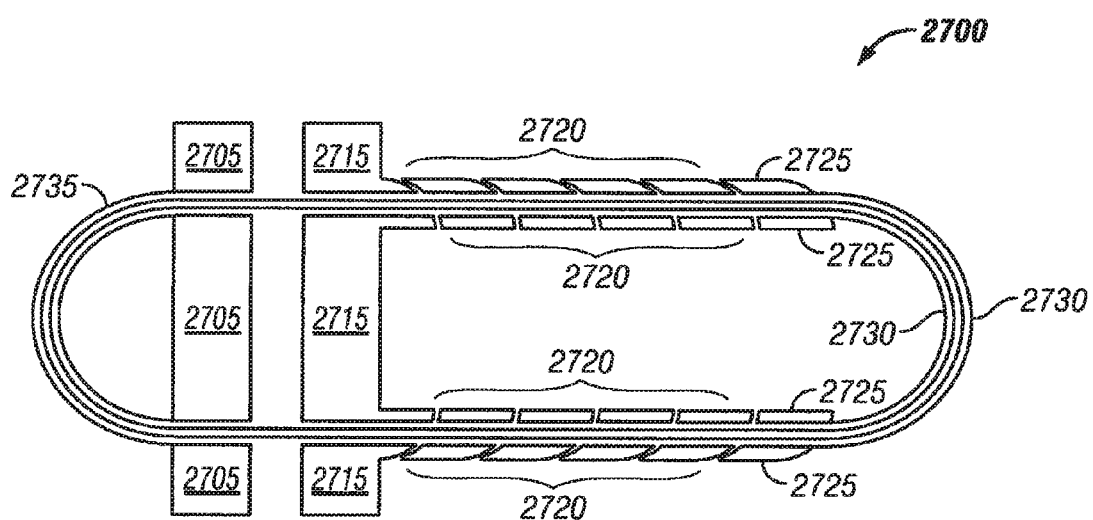
FIG. 27 depicts a rigidizable cannula with dual recirculation.

FIG. 27 shows a cross-sectional view of an embodiment of a cannula system 2700 with a rigidizable structure and dual recirculation. A static tension anchor 2705 is coupled to a proximal recirculation guide 2735 that houses a tensioning element 2710. The tensioning element 2710 may be a wire, filament, or multi-stranded cable. The tensioning element may also have a sheath or coating to improve its lubricity. The tensioning element passes through a dynamic tensioning anchor 2715, nested links 2720, terminal link 2725, and a recirculating guide 2730; thus linking them together. The tensioning element 2710 is not attached to any of the components of the cannula system 2700 and is able to slide freely through the dynamic tensioning anchor 2715, nested links 2720, proximal recirculating guide 2735, and distal recirculating guide 2730. This configuration creates the most flexible linkage as it shortens the recirculation distance for the tensioning cables to no more than ½ the length of the linkage.

In a preferred mode of operation, the cannula system 2700 is rigidized in a manner similar to that described for the cannula systems 2500 and 2600. The static tension anchor 2705 is held in a fixed position while the dynamic tension anchor 27615 is moved to compress the array of nested links 2720. Displacement of the distal end (distal recirculating guide 2730) is governed primarily by the elasticity and slack of the tensioning element 2710, whereas the shortening of the cannula system due to interlink gap closure and link deformation is accommodated by the displacement of the dynamic tension anchor 2715.

Figure 28:
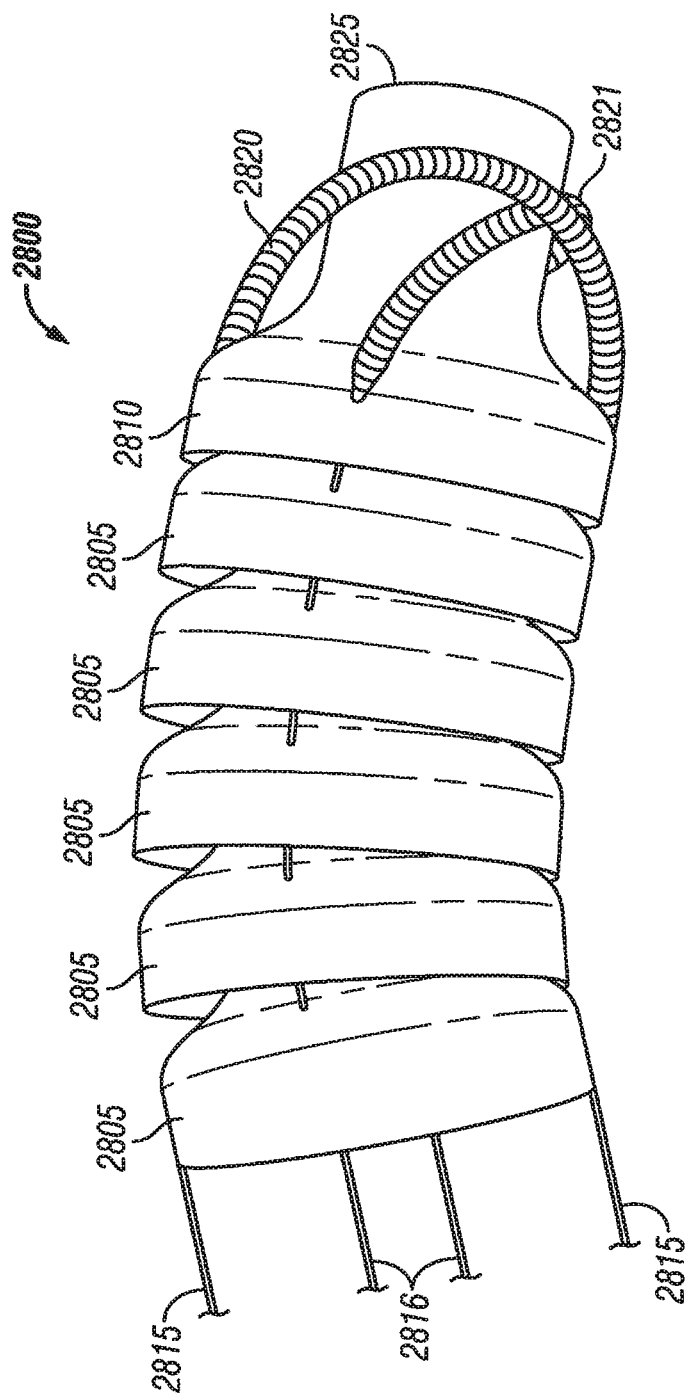
FIG. 28 depicts a rigidizable cannula wiper tip with distal recirculation.

FIG. 28 shows the distal end 2800 of an embodiment of a rigidizable cannula system similar to the cannula system 2500 of FIG. 25. In this embodiment, a tensioning element 2815 and a tensioning element 2816 traverse nested links 2805, wiper link 2810 and distal recirculating guides 2820 and 2821. Wiper link 2810 has a distal aperture 2825 that is narrower than that of the nested links 2805. The narrow aperture 2825 of the wiper link 2810 provides a close tolerance clearance for an inserted instrument that helps prevent the induction of material into the gap between the wiper link 2810 and an inserted instrument. The narrow aperture also provides better direction control over the tip of an inserted instrument as it is advanced.

Figure 29:
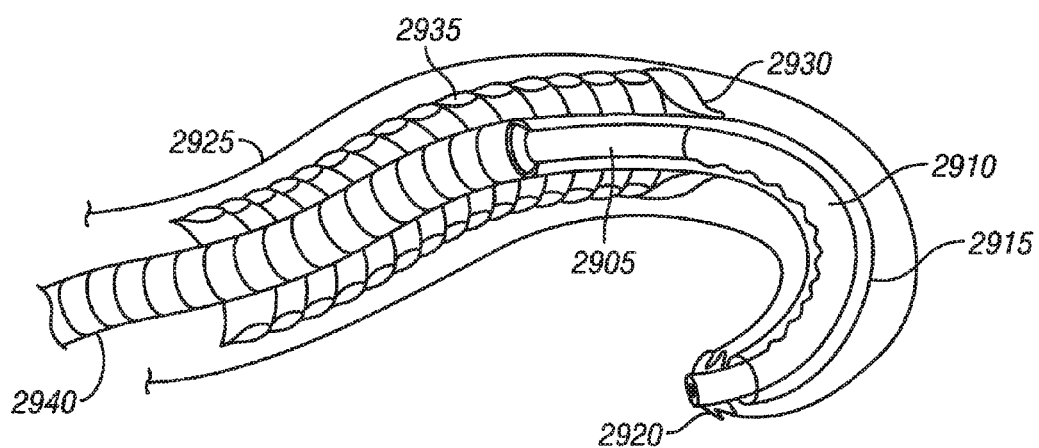
FIG. 29 depicts a for dual cannula system with an endoscope liner and external cover.

FIG. 29 shows an inner rigidizable linkage 2940 providing a conduit for an endoscope 2905 with a steerable tip 2910 coupled an endoscope tip liner 2915 by a gasket 2920. The endoscope tip liner 2915 provides a surface that allows the endoscope tip 2915 to slide freely within an outer rigidizable linkage 2935. In one embodiment the endoscope tip liner 2915 is constructed from helical mesh. The endoscope tip liner may be sized so that it fits within and fills a gap between a wiper link 2930 and the endoscope 2905. The gasket 2920 may also couple an external cover 2925 to the steerable tip 2910.

FIG. 30A shows an embodiment of a cannula system 3000 having an endoscope 3001 coupled to handles 3002 and 3010 that serve as support for two independent actuating systems. Handle 3010 supports static plate 3011 that is similar to static tension anchor 2505 of FIG. 25. Dynamic plate 3012 is similar to dynamic tension anchor 2515 of FIG. 25, and is coupled to static plate 3011 by actuators 3013 and 3014 (e.g., air cylinders). Dynamic plate 3012 is coupled to, and serves to compress an outer linkage 3020 that runs concentrically over rigidizable linkage 3015. Actuators 3013 and 3014 serve to axially separate static plate 3011 and dynamic plate 3012, thus providing the operation as described with respect to FIG. 25. Handle 3002 supports static plate 3004, which is in turn coupled to dynamic plate 3003 by actuators 3005 and 3006 (e.g., air cylinders). Actuators 3005 and 3006 serve to axially separate static plate 3004 and dynamic plate 3003, thus providing the operation as described with respect to FIG. 25. A cannula 3008 that includes a rigidizable linkage 3015 similar to 2520 of FIG. 25 is attached to dynamic plate 3003.

FIG. 30B shows the cannula system 3000 of FIG. 30A in a retracted configuration. Handle 3003 has been displaced with respect to handle 3010 so that a greater portion of the rigidizable linkage 3015 resides within outer linkage 3020.

FIG. 31A shows an embodiment of a cannula system 3100. A reference frame handle 3105 supports a static anchor plate 3125 that is coupled to actuators 3110 and 3115 (e.g., air cylinders). A rigidizable linkage 3130 is coupled to dynamic anchor plate 3120. Cannula system 3100 is similar to system 2500 of FIG. 25. Actuators 3110 and 3115 are inactive and the rigidizable linkage 3130 is in a relaxed state.

FIG. 31B shows the cannula system 3100 of FIG. 31A in a rigidized configuration. Actuators 3110 and 3115 are active, and the separation between static anchor plate 3125 and dynamic anchor plate 3120 is increased, thereby rigidizing the rigidizable linkage 3130.

The reference frame handle 3105 allows a user to establish the relative position of the endoscope 3101 and the rigidizable linkage 3130 to expose a length L1 of the tip of the endoscope 3101. L2 is the distance from the tip of the rigidizable linkage 3130 to the handle. L2 is essentially constant, whether the rigidizable linkage 3130 is in a relaxed or rigidized state. At. The rigidizable linkage 3130 may be rigidized without substantially altering L2, while essentially maintaining the exposed tip length L1 without having to adjust the position of endoscope 3101 during the rigidization process.

FIG. 32 depicts a flow diagram of a method for rigidizing a cannula system in conjunction with an endoscope. In step 3205 an endoscope is axially displaced with respect to a surrounding rigidizable cannula to expose a specific length of a tip of the endoscope. At the same time a relative position between a handle of the cannula system and the endoscope is established. In step 3210 actuators are activated to rigidize a cannula while maintaining the previously established exposed length of the endoscope tip and relative position between the handle of the cannula system and the endoscope.

Figure 33A:
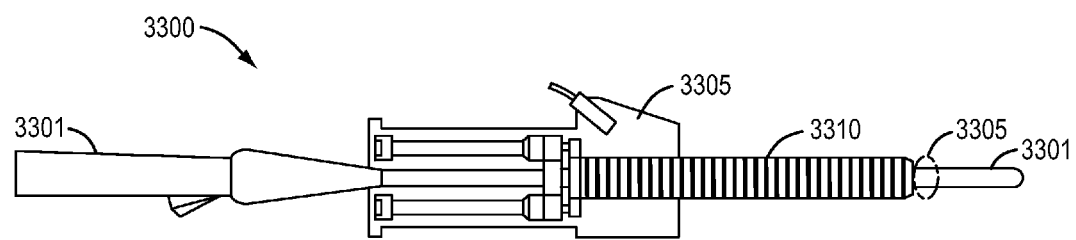
FIG. 33A depicts an endoscope with a cannula system including a distal inflatable balloon.

FIG. 33A shows an embodiment of a cannula system 3300 similar to that shown in FIG. 31A. A handle 3305 is coupled to a rigidizable linkage 3310 that acts as a conduit for an endoscope 3301. An inflatable balloon 3315 is coupled to the distal tip of rigidizable linkage 3310. While linkage 3310 is rigidized to support advancement of the endoscope 3301, the balloon 3315 may be inflated such that it engages a lumen, especially in mobile tissue such as the small bowel, so as to locally immobilize it such that endoscope 3301 may advance through the lumen efficiently. Balloon 3315 may then be deflated to advance linkage 3310 along endoscope 3301. Alternately, balloon 3315 may be used to hold the position of linkage 3310 relative to mobile tissue when linkage 3310 is relaxed for repositioning (e.g. for scope "straightening").

Figure 33B:
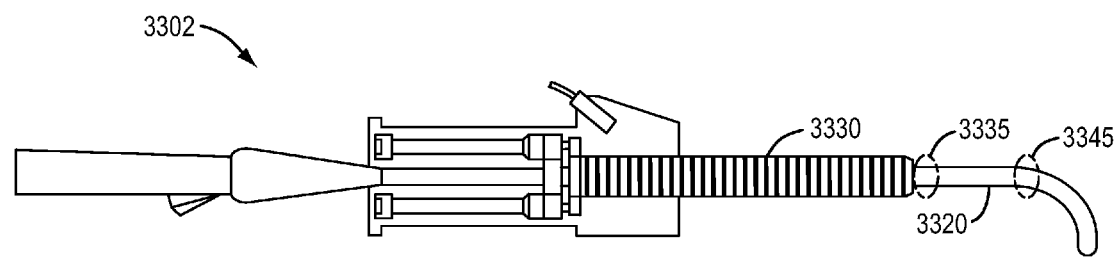
FIG. 33B depicts an endoscope with an inflatable balloon and a cannula system with a distal inflatable balloon.

FIG. 33B shows an embodiment of a cannula system 3302 that is similar to the cannula system 3300 shown in FIG. 33A, but whose rigidizable linkage 3330 serves as a conduit for endoscope 3320 that includes an inflatable balloon 3345. A balloon 3335 is coupled to the distal tip of the rigidizable linkage 3330 and a balloon 3345 is coupled to the endoscope 3320 proximal to the steering tip 3340. Balloon 3345 may be inflated to engage a lumen and hold position of mobile tissue such as the small bowel while the rigidizable linkage 3330 is made flexible and advanced over the endoscope 3320.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method of rigidizing a plurality of serial links, wherein the plurality of serial links extends as a cantilever from a supported proximal link to a distal link, the method comprising:
holding the distal link of the plurality of serial links in a substantially fixed position when the serial links are in a non-rigidized state, wherein the plurality of serial links are coupled together to articulate relative to one another in the non-rigidized state; and
rigidizing the serial links by moving all the serial links proximal of the distal link toward the substantially fixed position distal link.

2. The method of claim 1:
wherein holding the distal link in the substantially fixed position comprises statically anchoring the distal link at a proximal end of the serial links.

3. The method of claim 1:
wherein moving the serial links comprises moving a dynamic anchor toward the distal link.

4. The method of claim 1:
wherein rigidizing the serial links comprises applying tension to a tension element that is positioned in a recirculating guide at a distal end of the serial links.

5. The method of claim 1:
wherein rigidizing the serial links comprises applying tension to a tension element that is positioned in a recirculating guide at a proximal end of the serial links.

6. The method of claim 1:
wherein rigidizing the serial links comprises applying tension to a tension element that is positioned in a first recirculating guide at a proximal end of the serial links and in a second recirculating guide at a distal end of the serial links.

7. A method comprising:
positioning a static anchor at a proximal end of a plurality of serial links, the plurality of serial links being coupled together to articulate relative to one another;
anchoring a distal link in the plurality of serial links to the static anchor; and
positioning a dynamic anchor at the proximal end of the plurality of serial links, the dynamic anchor being positioned and configured to move toward the anchored distal link.

8. The method of claim 7:
wherein anchoring the distal link to the static anchor comprises positioning the distal link in a substantially fixed position.

9. The method of claim 8:
wherein the plurality of serial links are positioned and configured to move toward the anchored distal link.

10. The method of claim 7 further comprising:
positioning a tension element through the plurality of serial links, the tension element being positioned and configured to couple the serial links together.

11. The method of claim 10 further comprising:
positioning a recirculating guide at a distal end of the serial links; and
positioning the tension element through the recirculating guide.

12. The method of claim 10 further comprising:
positioning a recirculating guide at the proximal end of the serial links; and
positioning the tension element through the recirculating guide.

13. The method of claim 10 further comprising:
positioning a first recirculating guide at the proximal end of the serial links; positioning a second recirculating guide at a distal end of the serial links; and
positioning the tension element through the first and second recirculating guide.

14. An apparatus comprising:
a plurality of serial links comprising a proximal end, a distal end, a distal link at the distal end, and a plurality of proximal links proximal of the distal link;
a static anchor positioned at the proximal end of the plurality of serial links, the distal link being anchored to the static anchor; and
a dynamic anchor positioned at the proximal end of the plurality of serial links, the dynamic anchor being configured to move the plurality of proximal links toward the anchored distal link,
wherein the plurality of serial links are coupled together to articulate relative to one another.

15. The apparatus of claim 14:
wherein the anchored distal link is held in a substantially fixed position.

16. The apparatus of claim 14, further comprising:
a tension element positioned through the plurality of serial links, wherein the tension element is coupled to the static anchor.

17. The apparatus of claim 16, further comprising:
a recirculating guide positioned at the distal end of the serial links;
wherein the tension element is positioned in the recirculating guide.

18. The apparatus of claim 16, further comprising:
a recirculating guide positioned at the proximal end of the serial links;
wherein the tension element is positioned in the recirculating guide.

19. The apparatus of claim 16, further comprising:
a first recirculating guide at the proximal end of the serial links and a second recirculating guide at the distal end of the serial links;
wherein the tension element is positioned in the first and second recirculating guides.

20. A medical device comprising:
a plurality of serial links extending as a cantilever from a supported proximal link to a free space distal link; and
a tension element positioned through the plurality of serial links, there being a rigidized state and non-rigidized state of the links defined based on tension in the tension element;

wherein the serial links other than the distal link are configured to move toward the distal link to place the serial links in the rigidized state; and wherein the device is configured to keep the distal link in a substantially fixed position in the rigidized state and the non-rigidized state of the links, and wherein the plurality of serial links are coupled together to articulate relative to one another in the non-rigidized state.

21. The medical device of claim 20, further comprising:
a static anchor positioned at a proximal end of the serial links, wherein the tension element is coupled to the static anchor.

22. The medical device of claim 21, further comprising:
a dynamic anchor configured to move the serial links other than the distal link toward the distal link to place the serial links in the rigidized state.

23. The medical device of claim 22, further comprising:
a recirculating guide positioned at a distal end of the serial links, wherein the tension element is positioned in the recirculating guide.

24. The medical device of claim 22, further comprising:
a recirculating guide positioned at the proximal end of the serial links, wherein the tension element is positioned in the recirculating guide.

25. The medical device of claim 22, further comprising:
a first recirculating guide at the proximal end of the serial links and a second recirculating guide at a distal end of the serial links, wherein the tension element is positioned in the first and second recirculating guides.

26. The method of claim 1, further comprising:
positioning an instrument in a hollow lumen defined by aligned orifices of the plurality of serial links, the instrument being configured to extend past the substantially fixed position distal link.

27. The method of claim 26, further comprising:
extending the instrument past the substantially fixed position distal link; and controlling a relative position of the substantially fixed position distal link and the instrument while the instrument is extended past the substantially fixed position distal link.

28. The method of claim 26, further comprising:
maintaining a substantially constant relative position of the substantially fixed position distal link and the instrument extended past the substantially fixed position distal link while moving the serial links toward the substantially fixed position distal link.

29. The method of claim 4:
wherein rigidizing the serial links further comprises applying a tension to a second tension element that is positioned in a second recirculating guide at the distal end of the serial links.

30. The method of claim 7, further comprising:
positioning an instrument in a lumen defined by aligned orifices of the plurality of serial links, the instrument being configured to extend past the anchored distal link.

31. The method of claim 30, further comprising:
maintaining a substantially constant relative position of the anchored distal link and the instrument extended past the anchored distal link when the dynamic anchor is moved toward the anchored distal link.

32. The apparatus of claim 14, further comprising:
a lumen defined by aligned orifices of the plurality of serial links, the lumen being configured to receive an instrument to be advanced past the anchored distal link.

33. The apparatus of claim 32:
wherein an orientation of the anchored distal link controls an orientation of the instrument extended past the anchored distal link.

34. The medical device of claim 23, further comprising:
a second recirculating guide positioned at the distal end of the serial links; and
a second tension element positioned in the second recirculating guide.

* * * * *